(12) United States Patent
Quake et al.

(10) Patent No.: US 7,247,842 B1
(45) Date of Patent: *__Jul. 24, 2007__

(54) METHOD AND SYSTEM FOR SCANNING APERTURELESS FLUORESCENCE MIRCROSCOPE

(75) Inventors: Stephen R. Quake, San Marino, CA (US); Guillaume Lessard, Rochester, NY (US); Lawrence A. Wade, La Canada, CA (US); Jordan M. Gerton, Upland, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/180,976

(22) Filed: Jul. 12, 2005

(51) Int. Cl.
*H01J 3/14* (2006.01)
*H01J 40/14* (2006.01)
*H01J 5/16* (2006.01)

(52) U.S. Cl. .................... 250/234; 250/458.1
(58) Field of Classification Search ........... 250/234, 250/458.1; 356/72–73, 301, 318
See application file for complete search history.

(56) References Cited

U.S. PATENT DOCUMENTS

| | | | |
|---|---|---|---|
| 5,479,024 | A | 12/1995 | Hillner et al. |
| 6,002,471 | A | 12/1999 | Quake |
| 6,046,448 | A | 4/2000 | Sato et al. |
| 6,643,012 | B2 | 11/2003 | Shen et al. |
| 6,681,133 | B2 | 1/2004 | Chaiken |
| 6,850,323 | B2 | 2/2005 | Anderson |
| 6,953,927 | B2 * | 10/2005 | Quake et al. ............... 250/234 |
| 2002/0109082 | A1 | 8/2002 | Nakayama et al. |

OTHER PUBLICATIONS

Gersen et al., "Near-field effects in single molecule emission", *Journal of Microscopy*, vol. 202, Pt 2, May 2001, pp. 374-378.
Gersen et al., "Influencing the Angular Emission of a Single Molecule", *Physical Review Letters*, vol. 85, No. 25, Dec. 18, 2000, pp. 5312-5315.
Gerton et al., Tip-Enhanced Fluorescence Microcopy at 10 Nanometer Resolution, Department of Applied Physics, CALTECH, MC 128-95, Pasadena, CA, 2004.
Gerton et al., "Fluorescence Apertureless Near-field Optical Microscope for Biological Imaging", The 7th International Conference on Near-field Optics and Related Techniques, Aug. 11-15, 2002, p. 71.

(Continued)

*Primary Examiner*—Georgia Epps
*Assistant Examiner*—Patrick J. Lee
(74) *Attorney, Agent, or Firm*—Townsend and Townsend and Crew LLP

(57) ABSTRACT

Methods and systems for operating an apertureless microscope for observing one or more features to a molecular sensitivity on objects are described. More particularly, the method includes moving a tip of a probe coupled to a cantilever in a vicinity of a feature of a sample, which emits one or more photons at a detected rate relative to a background rate of the sample based upon the presence of the tip of the probe in the vicinity of the feature. The method modifies the detected rate of the feature of the sample, whereupon the modifying of the detected rate causes the feature of the sample to enhance relative to background rate of the feature.

12 Claims, 38 Drawing Sheets

OTHER PUBLICATIONS

Kawata et al., Feasibiltiy of Molecular-Resolution Fluorescence near-field Microscopy using Multi-Photon Absorption and Field Enhancement near a sharp tip, Journal of Applied Physics, vol. 85, No. 3, 1999.

Lessard et al., "A Scanning Apertureless Fluorescence Microscope", Department of Applied Physics, California Institute of Technology, Pasadena, California, pp. 1-8.

Sanchez et al, Near-Field Fluorescence Microscopy Based on Two-Photon Excitation with Metal Tips, Physical Review Letters, vol. 82, No. 20, 1999.

Yang et al., "An Apertureless Near-field Microscope for Fluorescence Imaging", *Applied Physics Letters*, vol. 76, No. 3, Jan. 17, 2000, pp. 378-380.

Bachelot et al., "Apertureless Near-field Optical Microscopy: A Study of the Local Tip Field Enhancement Using Photosensitive Azobenzene-Containing Films," *Journal of Applied Physics* (Aug. 1, 2003), vol. 94, No. 3, pp. 2060-2072.

Brody et al., "Self-Assembled Microlensing Rotational Probe," *Applied Physics Letters* (Jan. 4, 1999) vol. 74, No. 1, pp. 144-146.

Lessard et al., "Ultra High Resolution Optical Microscopy (SIAM)," The Quake Group, downloaded from Internet <<http://thebigone.caltech.edu/quake/research/siam.html>> on Apr. 9, 2002, 2 pages.

Furukawa et al., "Local Field Enhancement with an Apertureless Near Field Microscope Probe," *Optical Communications* (1998) vol. 148, pp. 221-224.

Hamann et al., "Enhance Sensitivity Near Field Scanning Optical Microscopy at High Spatial Resolution," *Applied Physics Letters* (Sep. 14, 1998) vol. 73, No. 11, pp. 1489-1471.

Hamann et al., "Near Field Fluorescence Imaging by Localized Field Enhancement Near a Sharp Probe Tip," *Applied Physics Letters* (Apr. 3, 2000) vol. 76, No. 14, pp. 1953-1955.

Zenhausern et al., "Apertureless Near-Field Optical Microscope," *Applied Physics Letters* (Sep. 26, 1994), vol. 65, No. 13, pp. 1623-1625.

Zenhausern et al., "Scanning Interferometric Apertureless Microscopy: Optical Imaging at 10 Angstrom Resolution," *Science* (Aug. 25, 1995), vol. 269. No. 5227, pp. 1083-1085.

* cited by examiner

- PLATINUM-IRIDIUM COATED TIPS (COMMERCIAL)
- 85-90% SUPPRESSION OF FLUORESCENCE
- PARTIAL RECOVERY OF FLUORESCENCE FOR *P*-POLARIZATION

SPECTRUM OF LASER FOR SAMPLE EXCITATION

TRANSMISSION SPECTRUM OF THE
"EXCITATION CLEAN-UP FILTER"

METHOD AND SYSTEM FOR SCANNING APERTURELESS FLUORESCENCE MIRCROSCOPE

STATEMENT AS TO RIGHTS TO INVENTIONS MADE UNDER FEDERALLY SPONSORED RESEARCH OR DEVELOPMENT

The U.S. government has rights in the disclosed invention pursuant to National Science Foundation Grant No. DMR-0080065 to the California Institute of Technology.

CROSS-REFERENCES TO RELATED APPLICATIONS

This application claims priority to U.S. patent application Ser. No. 10/616,896, filed on Jul. 9, 2003, which claims priority to U.S. Provisional Application No. 60/402,351, filed Aug. 9, 2002, which are incorporated by reference herein.

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The present invention relates generally to high resolution microscopy techniques. More particularly, the invention provides methods and systems for improved high resolution scanning using apertureless near field scanning optical microscopes ("ANSOM") that image one or more fluorescent samples with single photon excitation, which we call fluorescence ANSOM ("FANSOM"). But it would be recognized that the invention has a much broader range of applicability. For example, the invention can be applied with other types of images such as Raman scattering, and other multiphoton processes. Additionally, the samples can range from a variety of different fields such as electronics, semiconductor, organic chemistry, life sciences, biotechnology, micro and nanomachining and micro and nanodevices, molecular and biological circuits, and others.

Over the years, significant development of different types of microscopy has occurred. As merely an example, visible light optical microscopy using far field optics including lenses and light evolved from a simple compound microscope that is capable of resolving sizes of about 200 nanometers and greater. Examples of samples that are capable of being viewed using far field optics include biological cells and tissues, and are capable of being viewed using far field optics include biological cells and tissues, and others, which are often, bulk in nature. The resolving ability of such far field optical microscopy is generally limited by the diffraction of light. The diffraction limit for optical resolution has been stretched somewhat for far field imaging of very specific samples to perhaps 150 nanometers using confocal microscopes and other, related, approaches. Accordingly, atomic force microscopes ("AFM") and scanning optical microscopes including near field scanning optical microscopes were developed. The AFM and near field scanning optical microscopy ("ANSOM") have been developed to overcome certain limitations of far field optics. The AFM and near field scanning microscopes have also found many applications in biology, chemistry, physics, and materials science.

Near field scanning optical microscopy allows one to take optical images with resolutions below the diffraction limit of light. More particularly, light propagating through a waveguide is forced through a subwavelength aperture, which is then scanned in close proximity to a sample. Such subwavelength aperture techniques create other limitations. Here, physical limitations relate to a skin depth of the metal used to coat the waveguide and various scanning artifacts, which yield resolutions of 30 to 50 nanometers, most typically 50 to 100 nanometers. Apertureless near field scanning microscopes have been proposed and demonstrated to overcome these limitations, among others. Conventional ANSOM often involves using an oscillating sharp probe, which is scanned over the sample. The probe perturbs an incident laser beam, by introducing phase shifts in an electric field or by a periodic occlusion of the sample. Detection techniques are generally used to discriminate light scattered by near field interactions from a far field contribution. Limitations also exist with such ANSOM techniques. Such limitations include contaminated images based upon certain artifacts of the sample topography, and may include others.

A pioneering approach for achieving high resolution spectroscopic information using a scanning microscope is described in U.S. Pat. No. 6,002,471, assigned to California Institute of Technology, Pasadena, Calif., and in the name of Stephen R. Quake ("Quake"). Quake generally provides a system and method for obtaining high resolution spectroscopic information. The system generally includes a support and first optical elements for directing an optical beam at a sample, which is on the support. An optical element for collecting light emitted from the sample to reduce a background noise is also included. Other elements include a spectral dissociating apparatus, a probe, and a probe detection apparatus coupled to the probe. As merely an example, the probe enhances the light level emitted from the sample in the vicinity of the probe. Because this occurs only when the probe is in the immediate vicinity of the sample, detection of this modulation results in very high spatial resolution and chemical detection sensitivity. Fluorescence ANSOM, called FANSOM, has also been demonstrated. Conventional FANSOM often uses a principle of a two photon excitation and electric field enhancement near a tip of the probe. See, T. J. Yang, Guillaume A. Lessard, and Stephen R. Quake, An apertureless near field microscope for fluorescence imaging, Applied Physics Letters, Volume 76, Number 3, Jan. 17, 2000 ("Yang, et al."). Yang, et al. reports certain results achieved using the FANSOM designed to image fluorescent samples with single photon excitation. FANSOM has demonstrated resolutions in the 10-20 nm range. Although FANSOM appears to be promising, certain practical limitations may still exist.

From the above, it is seen that improved high resolution scanning techniques are desired.

BRIEF SUMMARY OF THE INVENTION

According to the present invention, techniques for high resolution scanning are provided. More particularly, the invention provides methods and systems for improved high resolution scanning using apertureless near field scanning microscopes that image one or more fluorescent samples with single photon excitation, which we call fluorescence ANSOM. But it would be recognized that the invention has a much broader range of applicability. For example, the invention can be applied with other types of images such as Raman scattering, multi-photon imaging techniques, and others. Additionally, the samples can be from a variety of different fields such as electronics, semiconductor, organic chemistry, life sciences, biotechnology and others.

In a specific embodiment, the invention provides a method for measuring characteristics of nanoscopic objects (e.g., 0.1 nanometers to >1,000 nanometers) using detection of photons emitted from the objects, e.g., Proteins or DNA tagged with fluorescent molecules. The method includes moving a tip of a probe coupled to a cantilever toward a feature of a sample to influence and/or modulate a rate of fluorescence from the feature of the sample. The method measures and/or compares the first intensity level of electromagnetic energy from a feature of a sample during a first predetermined portion of movement of the cantilever and records a change in the first intensity level to a second intensity level during a second predetermined portion of movement of the cantilever using a detector or the like.

In an alternative specific embodiment, the invention provides a system for measuring characteristics of nanoscopic objects using detection of photons emitted from the objects. The system has one or more computer memories, which include computer codes. A first code is directed to cause movement of a tip of a probe coupled to a cantilever member toward a feature of a sample to influence a detected rate of fluorescence from the feature of the sample. A second code is directed to apply illumination using a first intensity level of electromagnetic energy to the feature of the sample during a first predetermined portion of movement of the cantilever member to capture a signal from the feature at a detector from the sample. The one or more memories also include a third code directed to output a control signal to switch the first intensity level to a second intensity level during a second predetermined portion of movement of the cantilever member. Depending upon the embodiment, other computer codes can also be used to implement the functionality described herein as well as outside of this specification.

In a specific embodiment, the invention provides a capability to extend the lifetime of fluorescent molecules. Preferably, the method extends the life of such molecules by turning an excitation laser on only during specific periods of the data gathering cycle, which can improve and possibly maximizes a lifetime of the fluorescent molecule by delaying photobleaching or other similar features. Photobleaching is a photo-catalyzed chemical reaction that severely reduces or completely eliminates fluorescence emission. In addition this allows the signal to be maximized during imaging. Image scans often include series of fast probe movements, or line scans, along one axis and backcoupled with a slow continuous movement or discrete set of movements along the orthogonal axis of the sample surface plane-rastering pattern. Such rastering pattern continues until the desired portion of the sample plane is mapped which forms one image frame. The probe is typically made to oscillate rapidly (typically but not limited to 50-400 kilohertz oscillation frequency) up and down so that it lightly "taps" on the sample surface, following the sample topography while being rastered over the surface. When an image frame begins or ends, the probe controller sends a voltage signal that is monitored by the data acquisition computer. Similarly, the probe controller sends a voltage signal when each line scan begins in one direction and another signal at the beginning of the return movement. The image is typically constructed of either all-forward direction line scans or all return line scans in certain embodiments. If forward direction line scans are desired, then the controlling software detects the voltage pulse signaling the onset of forward scanning and in turn sends a voltage signal to an acousto-optic modulator that switches so that the excitation laser transmits into the FANSOM optical system. When the return line begins, a second voltage pulse is generated by the probe controller. As this line is not being used to create the image, the controlling computer stops sending the voltage pulse to the AOM. The AOM then switches so that the excitation laser light is no longer transmitted into the FANSOM optical system and the sample is not illuminated. This process repeats for each line with the sample being illuminated only during forward direction line scans. When the image frame is complete, the laser is commanded to switch off (in this case by stopping the voltage pulse to the AOM) until the initiation of the next image frame.

There can be other modifications, alternatives, and variations. As described above, the triggering of the laser switching can be actuated at the beginning of each line scan. Alternately it could begin based on topographical information from the probe (that is that the probe is over the sample of interest) or on a user defined area or coordinate set. The switching itself can be accomplished in a variety of ways other than the acousto-optical method described above. These other ways include using an electro-optic modulator or a shutter or chopper which is triggered or timed to correspond to the aforementioned inputs (beginning of line, coordinate, topographical information). The use of either an acousto-optic or electro-optic switching method allows for extremely fast (<10 nanosecond) switching times which enables other types of laser-triggering schemes. For instance, the laser may be triggered by the oscillating motion of the probe so that the laser would be on only for a portion of the probe oscillation cycle. This triggering scheme can be used to enhance the optical contrast as well as maximizing and/or improving the fluorescent molecule lifetimes. Other techniques may also use scanners, mirrors (e.g., MEMS), any combination of these and the like.oi In an alternative specific embodiment, the invention provides a method for operating an apertureless microscope for viewing microscopic features of objects to molecular sensitivity. The method includes aligning the excitation laser beam to a tip coupled to a cantilever through a probe or a portion of the cantilever within a first assembly. There are several methods for accomplishing such alignment to nanometric accuracy. Gross alignment within a few microns can be achieved by viewing the back reflection of the excitation laser beam and the cantilever laser illumination of the cantilever and either moving the cantilever assembly until the two beams are properly aligned. Alternately or in combination a tip-tilt mirror can be used to move the focus of the excitation laser so that it is properly aligned with the cantilever tip. Additionally, the shadow cast by the cantilever when illuminated by the excitation laser can be visualized or imaged and used to align the tip with the excitation laser. Fine alignment to approximately 1 micron and possibly less can be achieved by illuminating the cantilever with monochromatic light or broadband light such that the optics can image the cantilever tip shadow relative to the excitation laser. Piezoelectric actuators can be used to either move the tip until properly aligned with the excitation laser or to steer the excitation laser until it is properly aligned with the tip. Fine and ultrafine alignment to as little as a few nanometers can be achieved by imaging the backscatter of the excitation laser either when scanning the laser over the cantilever tip or alternately when scanning the tip over a fixed focus excitation laser. The backscatter image gives a high resolution image via the microscope objective which allows the relative positions of the tip and the laser to be established.

Final alignment can then be achieved by either moving the cantilever assembly, moving the cantilever tip or the excitation laser focus point until the excitation laser and the cantilever tip are properly aligned. All of the previously mentioned alignment steps can be carried out separately or in combination. Also they can be carried out in combination with a properly marked sample substrate which incorporates appropriate position reference points and or structures. Alignment can be maintained while imaging in several ways. It can be achieved by imaging the excitation laser back-reflection. The imaged diffraction pattern can then be used to monitor changes in relative position which can be used to correct any misalignments which develop if the laser tracks the cantilever tip while imaging a sample. Alternately, this imaged pattern information can be used to provide primary commands to move the excitation laser to track a moving cantilever tip. Finally, it can be used to correct other accumulated misalignments including but not limited to thermal drift and piezo and/or other mechanical strain relaxation, hysteresis, and piezo creep. These techniques can be used to achieve and maintain alignment whether the cantilever tip scans a stationary sample and excitation laser, both the cantilever tip and excitation laser scan a stationary sample, the excitation laser scans a stationary cantilever tip and sample, or a stationary cantilever tip and excitation laser scan a moving sample.

In yet an alternative embodiment, the invention provides an apertureless microscope system for viewing one or more features of samples to a resolution of molecular sensitivity. The system has a member for supporting the apertureless microscope system. A support structure is coupled to the member to support the member. A plurality of shock absorbing devices is coupling the support structure and the member. The plurality of shock absorbing devices is capable of substantially eliminating a possibility of mechanical noise from the floor structure. The system also has an enclosure structure coupled to the member and covering the apertureless microscope system. The enclosure houses the apertureless microscope within an opening confined within the enclosure structure. A sound absorbing member is coupled to the enclosure structure to substantially eliminate a possibility of acoustic noise from entering into the opening within the enclosure structure. An inner liner is also coupled within the opening of the enclosure structure to absorb one or more stray photons within the enclosure structure. The inner liner is generally capable of substantially preventing the stray photons from being released back into the enclosure structure.

Still further, the invention provides a method for operating a scanning system in a substantially noise free environment for viewing one or more features of samples to a resolution of molecular sensitivity. The method includes inserting a sample having a molecular feature on a stage of an apertureless microscope system, which has at least a scanning apparatus including a probe coupled to an optical imaging apparatus. The optical imaging apparatus is adapted to capture information having a feature size of less than five nanometers from a portion of the sample. The method also maintains at least the stage and the sample in an opening confined by an enclosure structure, which is coupled to a member for supporting a portion of the apertureless microscope system. The method maintains at least the stage and the sample free from mechanical vibration noise using a plurality of shock absorbing devices coupling the member. The plurality of shock absorbing devices is capable of substantially eliminating a possibility of mechanical vibration noise from an external source. The method further maintains at least the stage and the sample free from acoustic noise using a sound-absorbing member coupled to the enclosure structure to substantially eliminate a possibility of the acoustic noise from interacting with the captured information. A step of capturing one or more stray photons within the opening of the enclosure structure using an inner liner coupled within the enclosure structure to absorb the one or more stray photons within the enclosure structure is included. The inner liner is capable of substantially preventing the one or more stray photons from being released back into the opening of the enclosure structure.

In a specific embodiment, the invention provides a method for operating an apertureless microscope for observing one or more features to a molecular sensitivity on objects. The method includes moving a nanotube based tip of a probe coupled to a cantilever in the near vicinity of a feature of a sample or the sample relative to the nanotube based tip. In common with the previously described embodiments, the nanotube based tip will enhance contrast by interacting with the sample and the excitation light. The same mechanisms described earlier, that reduce the amount of fluoresced and/or detected fluoresced light and increased the amount of fluoresced light, will also occur with this tip in the proximity of the sample and/or illuminated by the excitation light. In addition other effects may serve to enhance contrast. In addition the resolution is increased due to the small diameter (typically 1-3 nm) of a single-walled nanotube. Preferably, the nanotube structure is single walled, although it may be multiwalled or has several single-walled tubes in a rope and/or bundle structure. Preferably, the term rope is a structure made of more than one strand of nanotube material, which may be twisted together or in any other aggregated geometric configurations according to certain embodiments. Additionally, enhanced contrast and resolution may occur through a quenching influence of the one or more photons. As merely an example, enhancement through quenching is shown in the first two (Y axis is photons/sec). The second figure shows, in one case, quenching and enhanced emission simultaneously (see also FIG. 19). This offers an opportunity for further improvement in resolution.

In an alternative specific embodiment, the invention provides an apertureless microscope system for observing one or more features to a molecular sensitivity on objects. The system comprises a nanotube based tip on a probe coupled to a cantilever operable to move in a vicinity of a feature of a sample. Metallization of the nanotube tip increases the contrast enhancement by increasing the amount of interaction between the tip and the sample and/or the tip and the excitation laser depending on the specifics of the excitation beam and sample. This metallization also increases the nanotube attachment strength to the tip.

In an alternative specific embodiment, the invention provides an apertureless microscope system for observing one or more features to a molecular sensitivity on objects. The system comprises a metallized DNA molecule which is attached to the cantilever tip. The small diameter and high conductivity of this invention enables contrast enhancement and high-resolution FANSOM imaging in a method similar to the nanotube tips.

In a specific embodiment, the invention provides a method for dynamically viewing an increased field of view based upon a smaller fixed field of view to capture an image of features of samples to molecular sensitivity. The method includes illuminating through a fixed lens using a beam a feature of a sample. The beam is directed toward at least one tip of a probe, which is in a vicinity of the feature of the sample. The method scatters a portion of the beam off a portion of the tip of the probe. The method also detects the scattered portion of the beam. The method then processes the scattered portion of the beam to determine a pattern to identify a relationship between the tip and the beam for spatial alignment between the tip and the beam. A step of adjusting a position of the beam used for illumination based upon at least the pattern to maintain a desired relationship between the tip and the beam is also included.

In an alternative specific embodiment, the invention provides a system for dynamically viewing an increased field of view based upon a smaller field of view to capture an image of features of samples to molecular sensitivity. The system has an electromagnetic energy source (in a specific embodiment this can be a laser), which is capable of emitting a beam. A fixed lens is coupled to the electromagnetic energy source. The fixed lens focuses the beam toward at least one tip of a probe, which is in a vicinity of a feature of a sample to scatter a portion of the beam off a portion of the tip of the probe. A detector is coupled to the fixed lens. The detector detects the scattered portion of the beam. A processor is coupled to the detector. The processor is adapted to process the scattered portion of the beam to determine a pattern to identify a relationship between the tip and the beam for a spatial alignment between the tip and the beam. An adjustment device is coupled to the processor. The adjustment device is adapted to adjust a position of the beam based upon at least the pattern to maintain a desired relationship between the tip and the beam.

In an alternative specific embodiment, the invention provides a scanning microscope for viewing one or more features of molecular scale and below. The system has a support stage for holding an object to be observed. A tip is coupled to a probe, which is configured within a vicinity of a feature of the object. An illumination source is directed to apply electromagnetic radiation from the illumination source to the tip of the probe. This illumination is used to determine the position of the cantilever tip over the sample. The system has a filter coupled to the object to substantially eliminate amplified spontaneous emission (ASE) from a power spectrum of the electromagnetic radiation. Preferably, such filter has a narrow transmission width to block ASE at wavelengths both shorter and longer than a central laser wavelength according to a specific embodiment. Alternately, such filter can be a long pass filter to block ASE with wavelengths shorter than the central laser wavelength. In an alternative embodiment, such filter can be a short pass to block ASE with wavelengths longer than the laser wavelengths longer than the central laser wavelength. The system also has an object illumination source coupled to the support to illuminate at least the feature of the object. Additional filters allow the blocking of the central cantilever illumination and also of the excitation illumination. Finally a filter is used to remove ambient illumination outside the sample fluoresced wavelength(s). These filters serve to block the several sources of photons not emitted by the sample but are highly transmissive in the wavelengths emitted by the sample. In combination, the present filters allow signals at wavelengths longer than the central laser wavelength or shorter than the central laser wavelength to be observed according to a specific embodiment. A detector is coupled to the object to capture signals from at least the feature of the object. The signals are derived from a detection band from the object illumination source.

Many benefits are achieved by way of the present invention over conventional techniques. For example, the present technique provides an easy to use process that relies upon conventional technology. The invention can also provide improved resolution within a predetermined range of spatial feature sizes. Preferably, the invention can be applied to capture images from biological molecules and the like. Depending upon the embodiment, one or more of these benefits may be achieved. These and other benefits will be described in more throughout the present specification and more particularly below.

Various additional objects, features and advantages of the present invention can be more fully appreciated with reference to the detailed description and accompanying drawings that follow.

DETAILED DESCRIPTION OF THE INVENTION

According to the present invention, techniques for high resolution scanning are provided. More particularly, the invention provides methods and systems for improved high resolution scanning using apertureless near field scanning microscopes that image one or more fluorescent samples with single photon excitation, which we call fluorescence ANSOM microscope. But it would be recognized that the invention has a much broader range of applicability. For example, the invention can be applied with other types of images such as Raman scattering, multiphoton imaging techniques, and others. Additionally, the samples can be from a variety of different fields such as electronics, semiconductor, organic chemistry, life sciences, biotechnology, and others.

Figure 1:
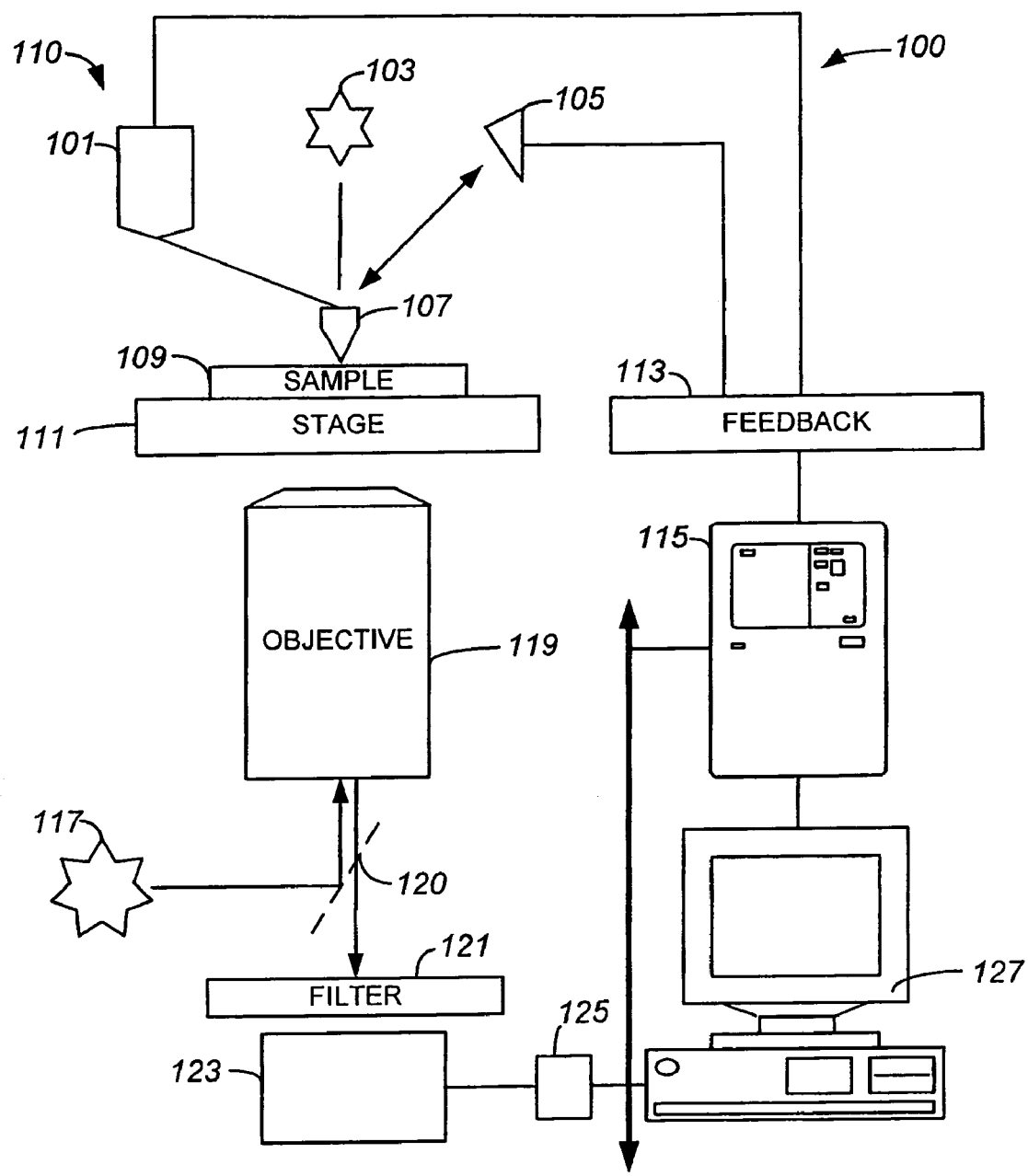
FIG. 1 is a simplified diagram of a scanning system 100 according to an embodiment of the present invention.

FIG. 1 is a simplified diagram of a scanning system 100 according to an embodiment of the present invention. This diagram is merely an example, which should not unduly limit the scope of the claims herein. One of ordinary skill in the art would recognize many other modifications, alternatives, and variations. As shown, the present microscope system 100 includes a mobile stage 111, which has x-y-z movement capability. The stage can be moved with a tolerance of less than 40 microns for sample positioning and when used for alignment can be moved with a tolerance of <1 nm. A sample 109 is placed on the stage. Depending upon the application, the sample can include a biological sample, a quantum dots, fluorescently tagged molecules, and Fluorescently tagged nano- or micro-structures, arrays or components. Preferably, the sample can also be in liquids, air, inert gas environments, or in vacuum and at specific temperatures (cryogenic, room temperature, warm to extremely high temperatures), depending upon the application.

The system also includes a tapping mode atomic force microscope ("AFM") 110. In a specific embodiment, the AFM 110 has various elements such as probe 107, a cantilever to support the probe, which is coupled to a piezoelectric stack 104. Such piezo-stack provides for dithering and z-motion of the cantilever. The AFM also includes a driving signal, which is coupled to control electronics 113 for signal detection and correction. Preferably, probe 107 has a pyramidal shape and the tip of the pyramid is coated with silver particles. Alternatively, other particles or coatings can also be used. For example, such coatings include, among others, semiconductor (e.g., silicon, silicon nitride, diamond, etc.), conductors (e.g., platinum, gold, silver alloys, aluminum, platinum-iridium, cobalt and any other metals as well as materials doped to be conductive), as well as combination of these, and the like. The AFM also includes a laser source 103, which is directed to the cantilever or probe. The laser source is used as a position detector, which provides photons that scatter off of the cantilever and/or probe. Such scattered photons are detected by way of photodetector 105, which is coupled to control electronics 113. The AFM is coupled to an inverted optical microscope, as shown.

Preferably, the inverted optical microscope 119 is underlying the AFM, as shown. A laser beam 117 (which in a specific embodiment is from a green HeNe 103 source) is focused on the AFM tip. The laser beam is directed from the source 117 and is adjusted by way of dichroic mirror 120 through the objective 119, which focuses the beam onto the AFM tip. As the sample is scanned in the x-y plane (which is also in the plane of the paper), fluorescent photons emit from the sample. Such photons pass through the objective through a bandpass filter 121 and are detected by an avalanche photodiode 123. A gated photon counter 125, which is coupled to the photodiode, processes the detected photons. The gated photon counter is triggered by a measured height of an AFM cantilever. A signal acquisition and processing apparatus 115 (which includes a microprocessor device and has been used as a "controller" and/or "main controller" herein without unduly limiting the scope of the term processing apparatus), which may be coupled to the counter through a common bus, oversees and performs operation and processing of information. The system also has a display 127, which can be a computer, coupled to the signal acquisition and processing apparatus. The signal acquisition and processing apparatus is also coupled to the control electronics of the AFM as shown.

In a specific embodiment, the AFM operates using a sinusoidal diving signal coupled to the AFM probe via the piezo-electric stack. The AFM probe is scanned over the surface of the sample, receiving the perturbations caused by the surface of the sample and transmitting the perturbed signal to the position detector. The position detector transmits a position signal to electronic systems for correcting and digitizing the signal. The correction occurs by comparing the position signal to an external height reference signal. The corrected AFM signal and the optical signal are coupled to the digitizing system for the processing of the AFM image of the surface topography and the optical image. Of course, there can be other modifications, alternatives, and variations. Further details of the present system can be found in the Quake patent, which has been previously described. Other details of the present system and methods are provided throughout the specification and more particularly below.

Figure 2:
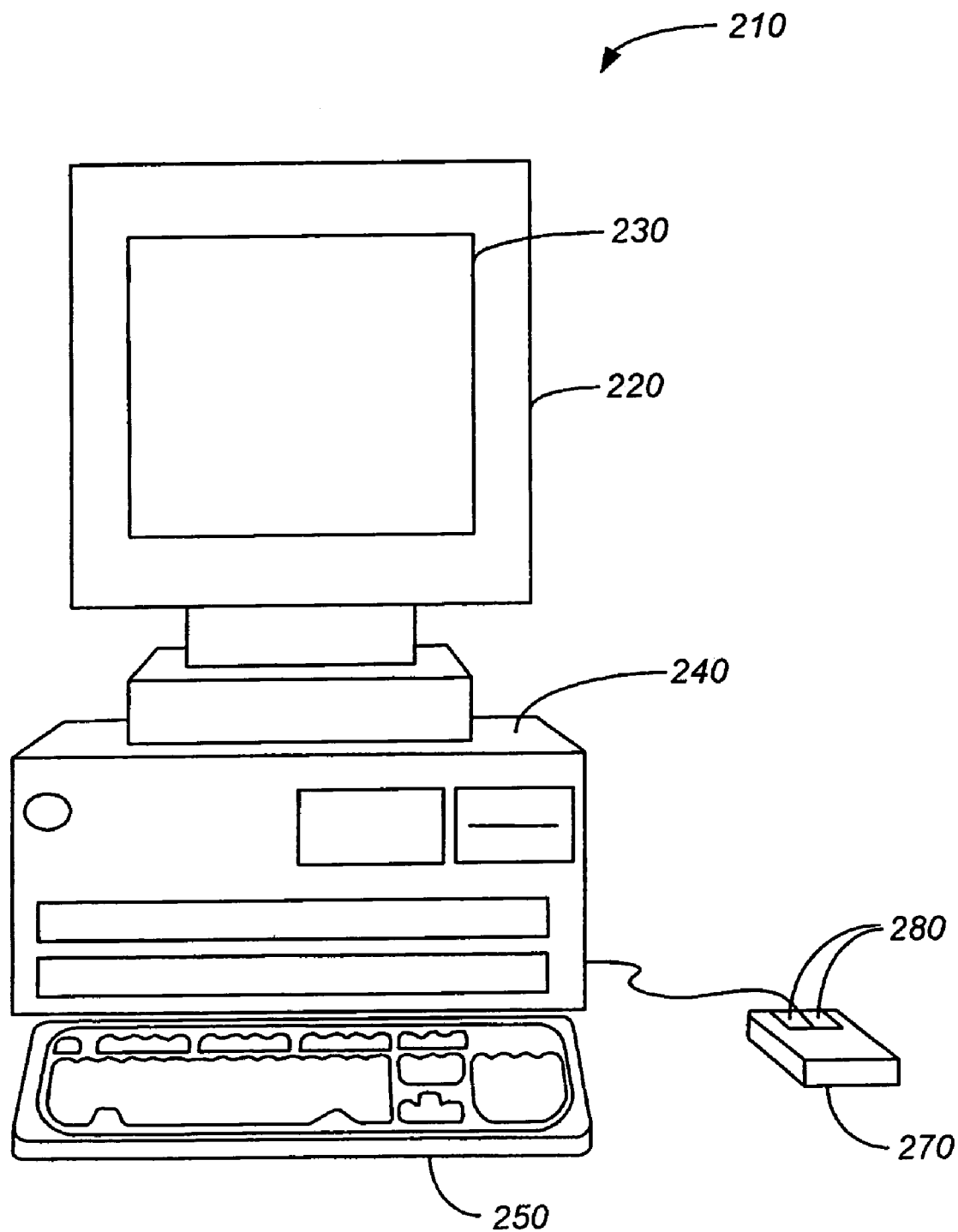
FIG. 2 is a simplified diagram of a computer system that is used to oversee the system of FIG. 1 according to an embodiment of the present invention.

FIG. 2 is a simplified diagram of a computer system 210 that is used to oversee the system of FIG. 1 according to an embodiment of the present invention. This diagram is merely an example, which should not unduly limit the scope of the claims herein. One of ordinary skill in the art would recognize many other modifications, alternatives, and variations. As shown, the computer system 210 includes display device 220, display screen 230, cabinet 240, keyboard 250, scanner and mouse 270. Mouse 270 and keyboard 250 are representative "user input devices." Mouse 270 includes buttons 280 for selection of buttons on a graphical user interface device. Other examples of user input devices are a touch screen, light pen, track ball, data glove, microphone, and so forth.

The system is merely representative of but one type of system for embodying the present invention. It will be readily apparent to one of ordinary skill in the art that many system types and configurations are suitable for use in conjunction with the present invention. In a preferred embodiment, computer system 210 includes a Pentium™ class based computer, running Windows™ NT operating system by Microsoft Corporation. However, the system is easily adapted to other operating systems and architectures by those of ordinary skill in the art without departing from the scope of the present invention. As noted, mouse 270 can have one or more buttons such as buttons 280. Cabinet 240 houses familiar computer components such as disk drives, a processor, storage device, etc. Storage devices include, but are not limited to, disk drives, magnetic tape, solid-state memory, bubble memory, etc. Cabinet 240 can include additional hardware such as input/output (I/O) interface cards for connecting computer system 210 to external devices external storage, other computers or additional peripherals, which are further described below.

Figure 2A:
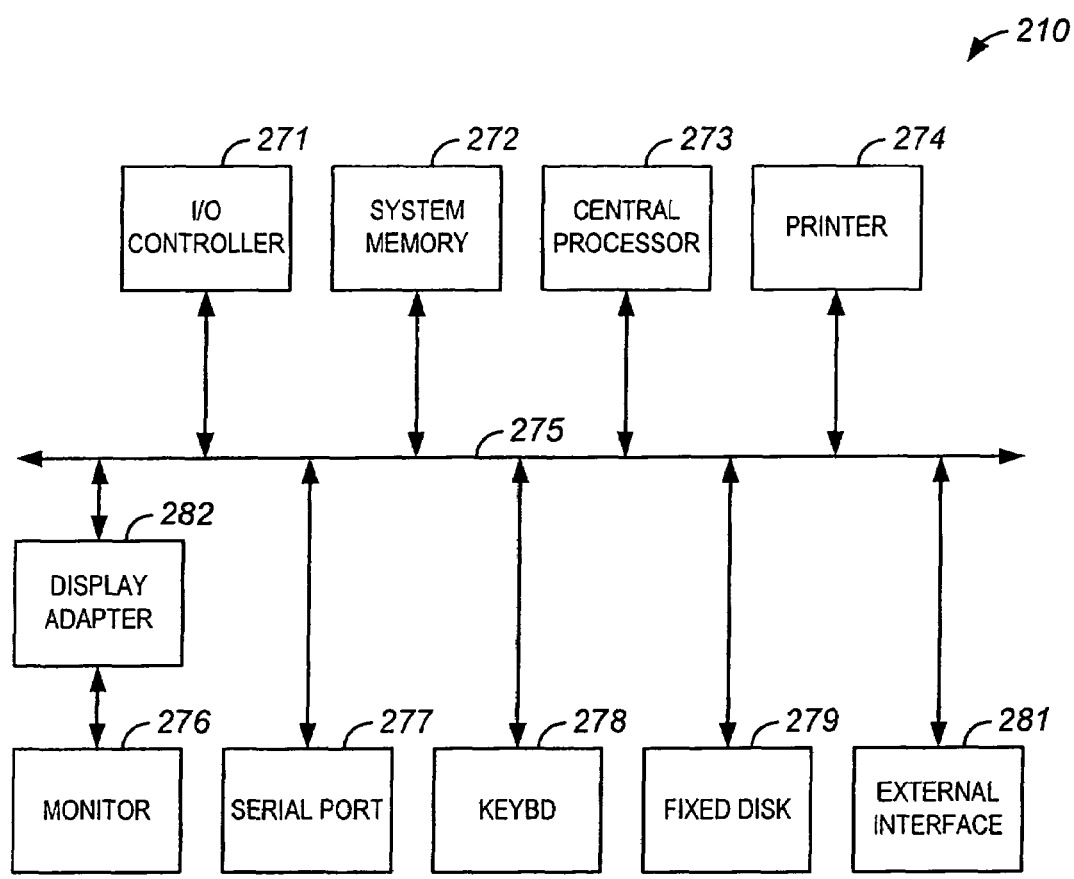
FIG. 2A is a more detailed diagram of hardware elements in the computer system of FIG. 2 according to an embodiment of the present invention.

FIG. 2A is a more detailed diagram of hardware elements in the computer system of FIG. 2 according to an embodiment of the present invention. This diagram is merely an example, which should not unduly limit the scope of the claims herein. One of ordinary skill in the art would recognize many other modifications, alternatives, and variations. As shown, basic subsystems are included in computer system 210. In specific embodiments, the subsystems are interconnected via a system bus 275. Additional subsystems such as a printer 274, keyboard 278, fixed disk 279, monitor 276, which is coupled to display adapter 282, and others are shown. Peripherals and input/output (I/O) devices, which couple to I/O controller 271, can be connected to the computer system by any number of means known in the art, such as serial port 277. For example, serial port 277 can be used to connect the computer system to a modem 281, which in turn connects to a wide area network such as the Internet, a mouse input device, or a scanner. The interconnection via system bus allows central processor 273 to communicate with each subsystem and to control the execution of instructions from system memory 272 or the fixed disk 279, as well as the exchange of information between subsystems. Other arrangements of subsystems and interconnections are readily achievable by those of ordinary skill in the art. System memory, and the fixed disk are examples of tangible media for storage of computer programs, other types of tangible media include floppy disks, removable hard disks, optical storage media such as CD-ROMS and bar codes, and semiconductor memories such as flash memory, read-only-memories (ROM), and battery backed memory.

Although the above has been illustrated in terms of specific hardware features, it would be recognized that many variations, alternatives, and modifications can exist. For example, any of the hardware features can be further combined, or even separated. The features can also be implemented, in part, through software or a combination of hardware and software. The hardware and software can be further integrated or less integrated depending upon the application. Further details of the functionality of the present invention can be outlined below according to the Figures.

Figure 3:
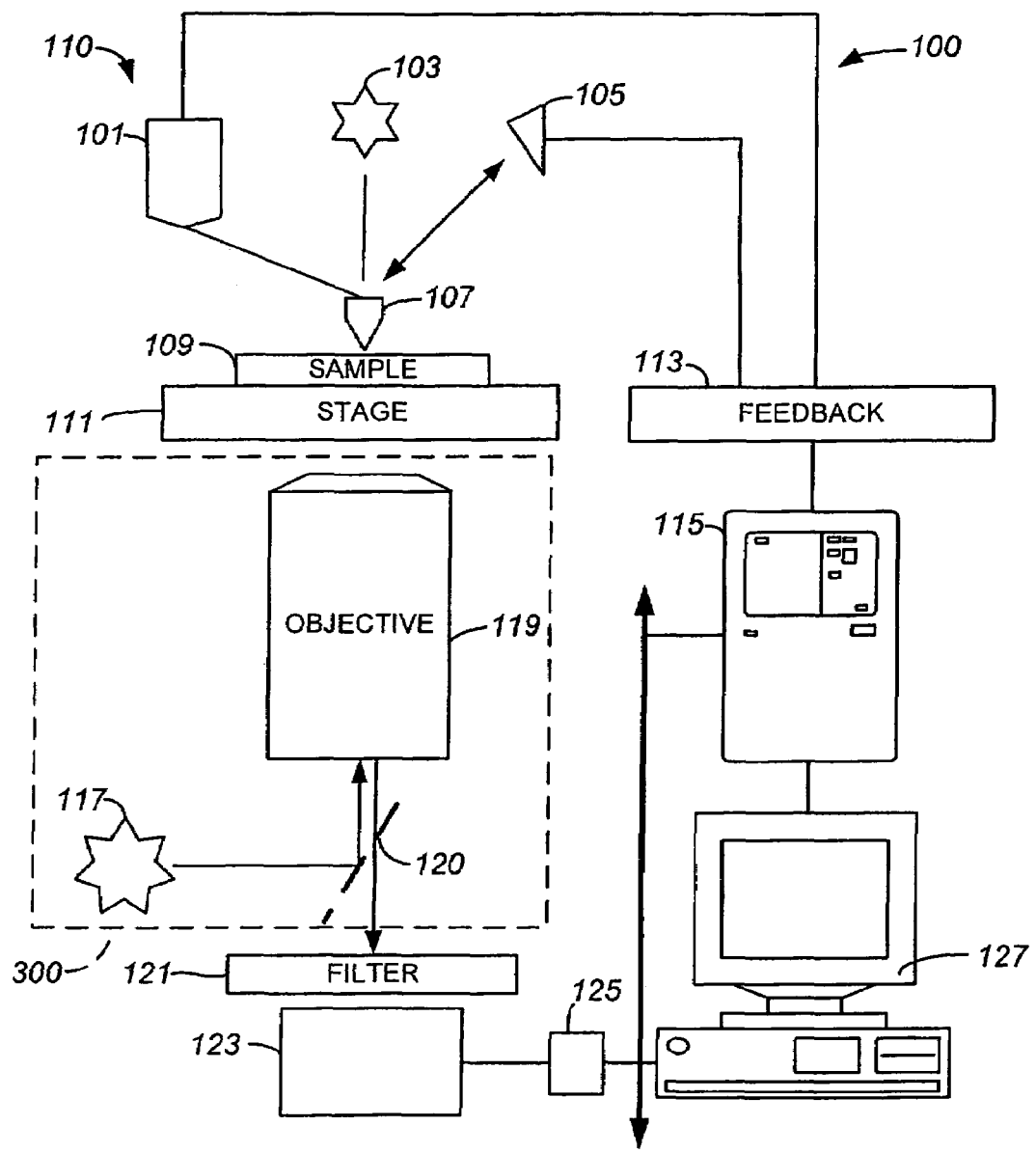
FIG. 3 is a simplified diagram of an improved illumination system for a scanning system according to an embodiment of the present invention.

FIG. 3 is a simplified diagram of an improved illumination system 300 for a scanning system according to an embodiment of the present invention. This diagram is merely an example, which should not unduly limit the scope of the claims herein. One of ordinary skill in the art would recognize many other modifications, alternatives, and variations. Like reference numerals are used in FIG. 3 as certain other figures herein, but ware not intended to be limiting. As shown, the present microscope system 100 includes mobile stage 111, which has x-y-z movement capability. The system also includes atomic force microscope ("AFM") 110. which is preferably a tapping mode atomic force microscope, but may also be others. In a specific embodiment, the AFM 110 has various elements such as probe 107, a cantilever to support the probe, which is coupled to a piezo-electric stack 104. Such piezo-stack provides for dithering and z-motion of the cantilever. The AFM also includes a driving signal, which is coupled to control electronics 113 for signal detection and correction. The AFM also includes a laser source 103, which is directed to the cantilever or probe. The laser source is used as a position detector, which provides photons that scatter off of the cantilever and/or probe. Such scattered photons are detected by way of photodetector 105, which is coupled to control electronics 113. The AFM is coupled to an inverted optical microscope, as shown.

The inverted optical microscope 119 is underlying the AFM, as shown. The laser beam 117 from the green HeNe 103 source is focused on the AFM tip. The laser beam is directed from the source 117 and is adjusted by way of dichroic mirror 120 through the objective 119, which focuses the beam onto the AFM tip. The system also has the bandpass filter 121 and avalanche photodiode 123. The gated photon counter 125 processes the detected photons. The gated photon counter is triggered by a measured height of the AFM cantilever. Signal acquisition and processing apparatus 115, which may be coupled to the counter through a common bus, oversees and performs operation and processing of information. Other features are also included.

Preferably, the system includes illumination system 300 that selectively adjusts an illumination level. Here, a shutter and/or a modulator material can selectively adjust the beam 117 from a first state to a second state. The first state can correspond to an on-state and the second state can correspond to an off-state. The on-state allows the beam to traverse through the modulator material. The off-state blocks the beam. As merely an example, a blocking material or filter can be used between the beam 117 and mirror 120. Such blocking material can include, among others, a modulator material. The modulator material can be coupled to the processing apparatus through the bus. Preferably, the modulator material is an acousto-optic ("AO") modulator, which will be described in more detail below. Of course, there can be other modifications, alternatives, and variations. For example, the modulator material can be replaced with a mechanical shutter, an electro-optic modulator, any combination of these, and the like.

Figure 3A:
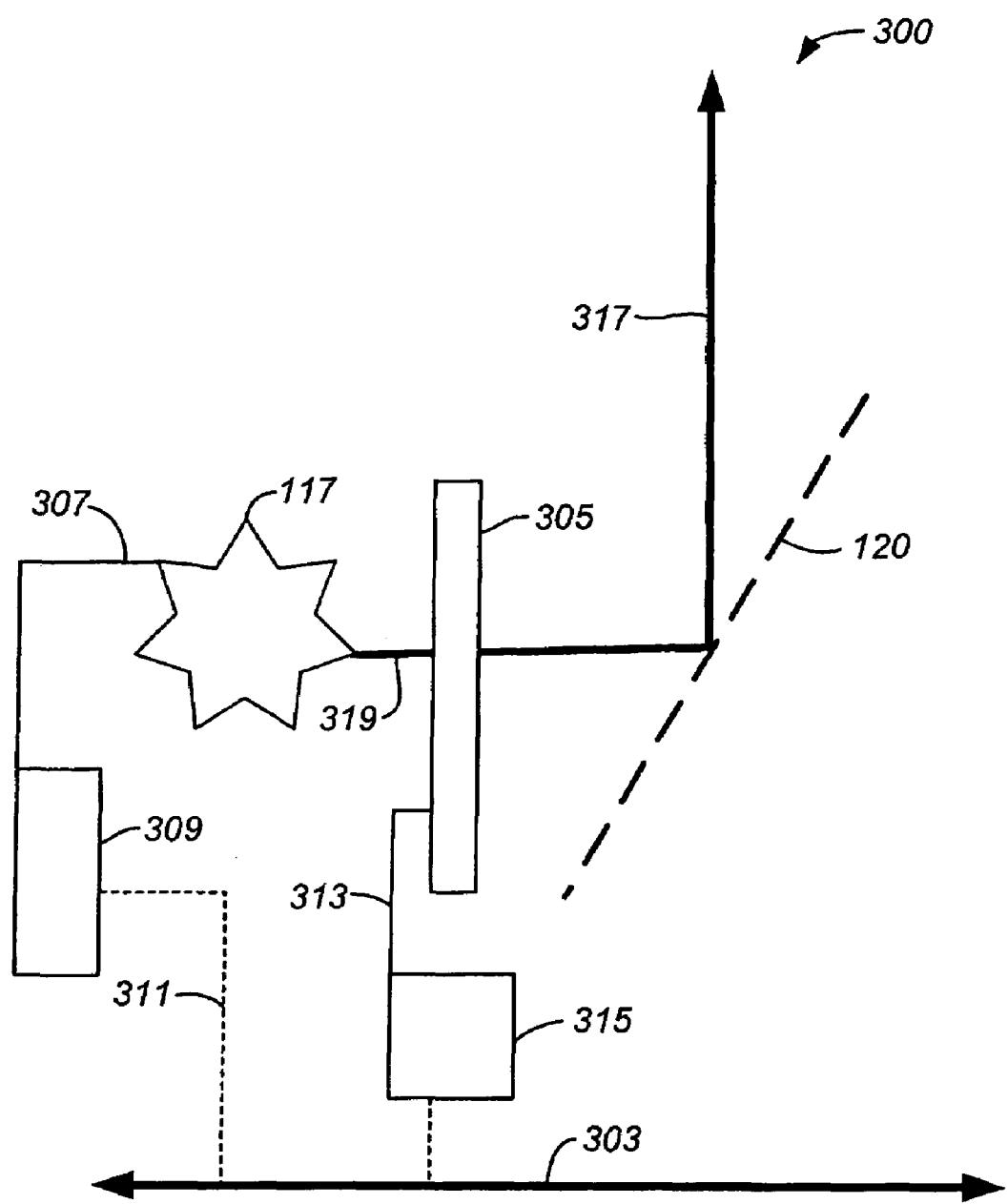
FIG. 3A is a more detailed diagram of the improved illumination system according to an embodiment of the present invention.

FIG. 3A is a more detailed diagram of the improved illumination system according to an embodiment of the present invention. This diagram is merely an example, which should not unduly limit the scope of the claims herein. One of ordinary skill in the art would recognize many other modifications, alternatives, and variations. As shown, the system includes common elements from other figures herein without unduly limiting the scope of the invention. The illumination system 300 includes laser beam 117 coupled to the objective through dichroic mirror 120. An AO modulator 305 is coupled between the beam and mirror in a specific embodiment. The modulator is made of suitable material to diffract the beam upon command such that it is no longer coupled into the fiber optic cable, thereby blocking transmission to the sample. An example of such a material is lead molybate. The material also has to have a certain speed characteristic. That is, the modulator material should be able to change states within 0.1 milliseconds seconds and less. Preferably, the modulator material changes where the light is bent in a different direction which no longer corresponds to the fiber, i.e., the modulator is in fact blocked. An example of such a material is from ISOMET Corporation: According to a specific embodiment, when aligned at the Bragg angle which correctly corresponds to the laser wavelength and RF frequency being applied, the modulator material diffracts a portion of the beam passing through it (zeroth order) into an adjacent location (first order). The first order beam is normally used for most applications. The intensity of the first order light is controlled by the amplitude of the RF signal. Either digital (on-off) or analog (video) modulation of the first order spot can be produced, depending on the type of driver selected. Of course, the type of material used depends upon the application.

The modulator is coupled to input/output device 315 through line 313. The input/output device may also include driving circuits, depending upon the application. Alternatively, the modulator has integrated driving circuits. Laser beam 117 is coupled to input/output device 309 and is also coupled to bus 303, which connects to the processing apparatus. Similarly, input/output device 315 couples to bus 303, which connects to the processing apparatus. A simple switching method can be provided using the present system.

In a specific embodiment, the modulator includes at least two states corresponding to an on-state and an off-state. In an on-state, the modulator allows beam 319 to traverse through the modulator material and reflect off of mirror 120 to enter 317 into the objective. As merely an example, the modulator material is in a transparent state, which allows the beam to traverse therethrough. Alternatively, the modulator material can be in the off-state, where the terms "off" and "on" are merely be used for descriptive purposes without limiting the scope of the claims herein. In the off-state, the modulator/optical assembly material blocks beam 319 and does not allow beam 317 to traverse therethrough (not shown). In a specific embodiment, the processing apparatus oversees the operation of the modulator material in reference to the operation of the present methods described herein as well as outside of this specification. Of course, there can be other modifications, alternatives, and variations. For example, the modulator material can be replaced with a mechanical shutter, an electro-optic modulator, any combination of these, and the like. The modulator is preferred in most embodiments (rather than adjusting the laser beam that should often be stabilized before use in the present method and system). Other details of the present system and methods are provided throughout the specification and more particularly below.

An illumination method used for operating the scanning apparatus according to an embodiment of the present invention is provided as follows.

1. Begin process for scanning using FANSOM a feature of an object;
2. Initiate line scan process for a line along a first direction (which is different from a second direction to be described below);
3. Transfer control signal from probe controller to main controller at beginning the scan along the first direction;
4. Determine if an image is to be constructed using the main controller;
5. If the image is to be constructed, send signal from main controller to modulator to allow beam to traverse through the modulator;
6. Illuminate the feature of the object while capturing information for the image of the feature;
7. Complete scanning of the object in the first direction while constructing the image of the feature;
8. Transfer control signal from probe to controller with beginning a scan along a second direction, which is different from the first direction;
9. Determine if an image is to be constructed;
10. If the image is to be constructed along the first direction, send signal from controller to modulator to allow beam to traverse through the modulator;
11. Alternatively, send signal (or no signal) form the controller to the modulator to prevent beam from traversing through the modulator;
12. Illuminate the feature of the object or maintain the object without illumination depending upon steps 10 and 11;
13. Complete scanning in the second direction; and
14. Perform other steps as desired.

As shown, the present method provides ways to turn on and turn off illumination of a beam used for a feature of an object. In a specific embodiment, the process repeats for each line with the feature of the object being illuminated only during left to right scans as an image is built up. Once the image is complete, the laser is commanded to switch off (in this case by stopping the signal to the modulator) until initiation of the next image scan. Further details of this method are described according to the Figures below.

Figure 4:
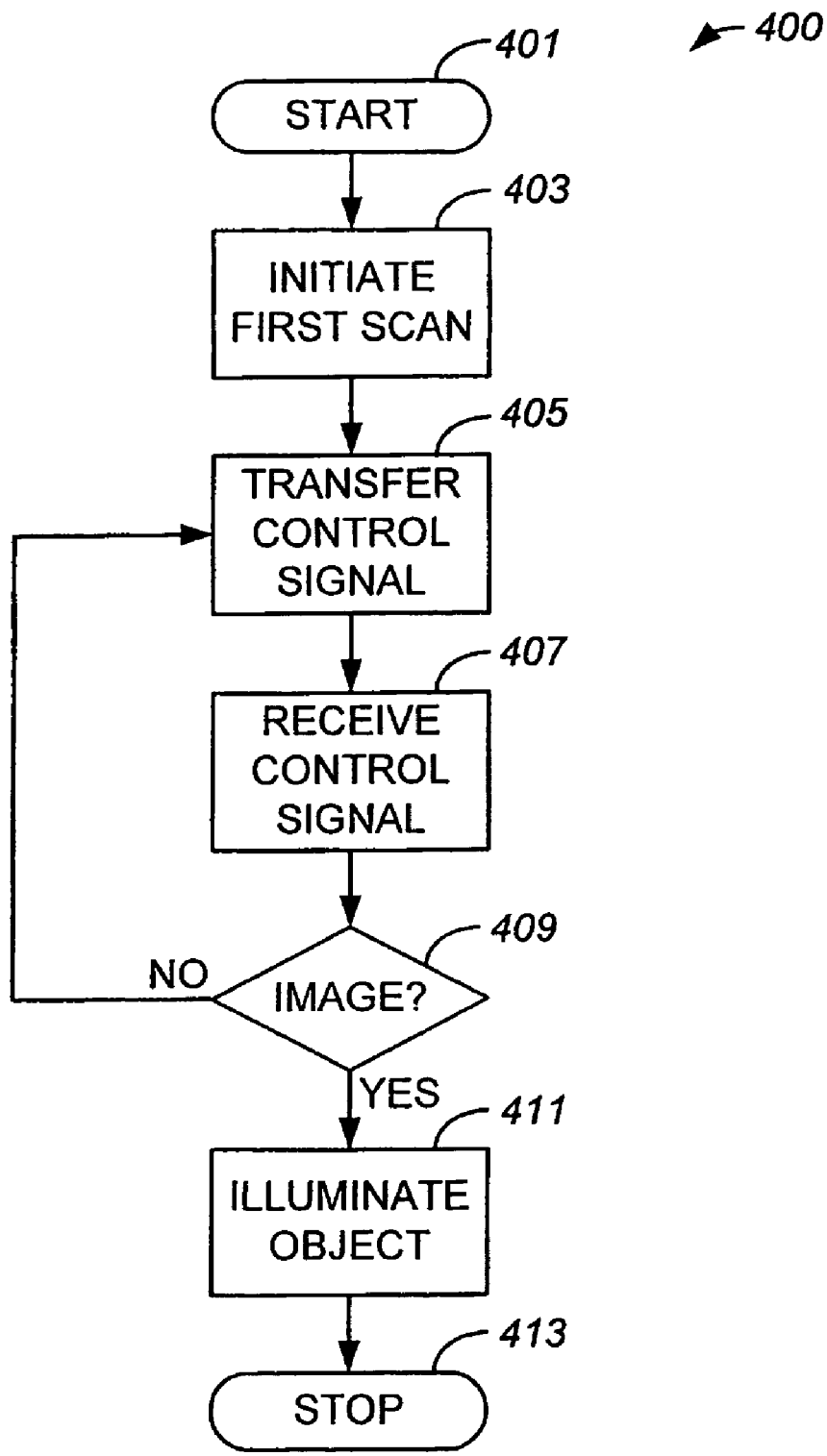
FIGS. 4 through 5 are simplified diagrams of scanning methods according to embodiments of the present invention.
Figure 5:
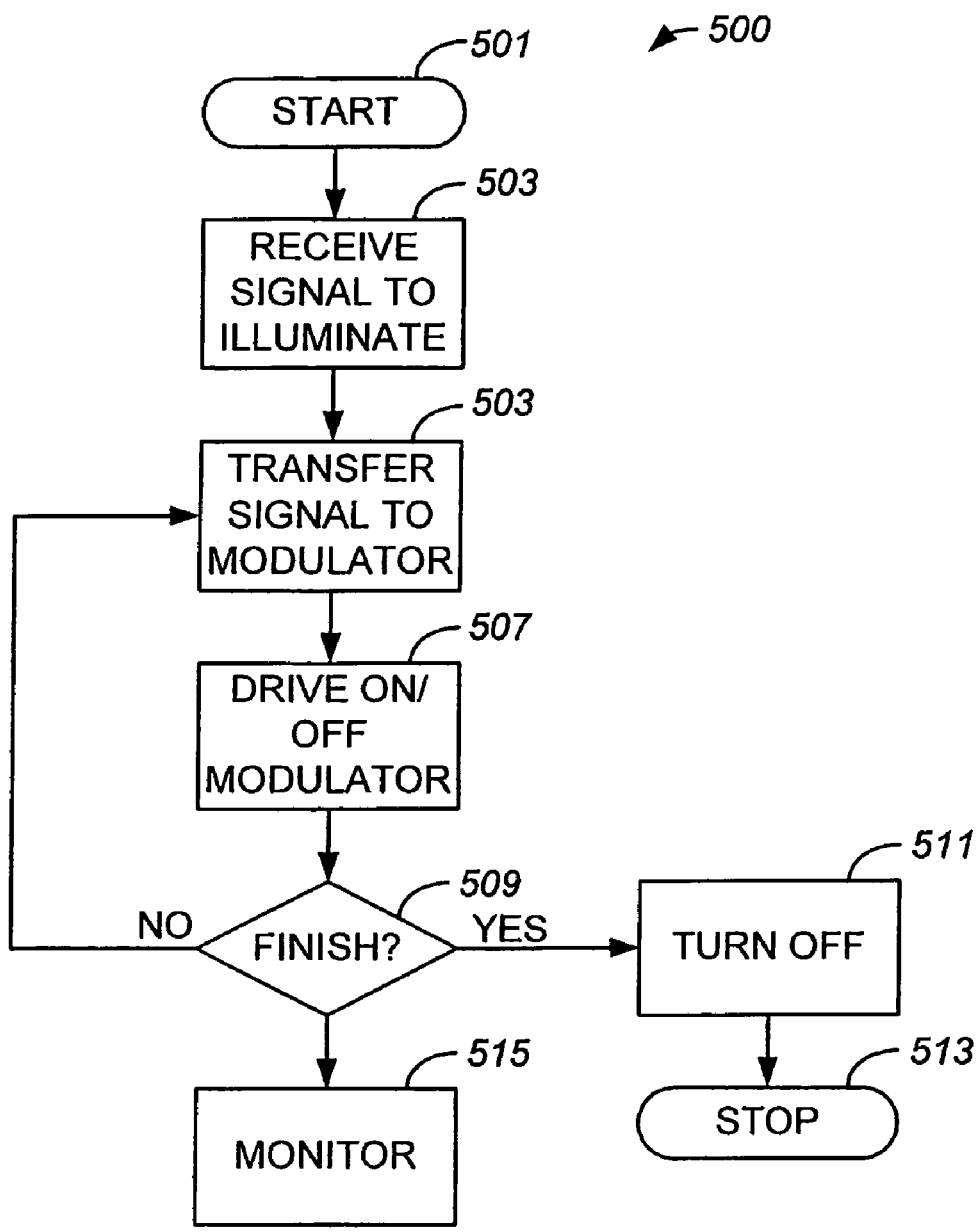

FIGS. 4 through 5 are simplified diagrams of scanning methods 400, 500 according to embodiments of the present invention These diagrams are merely examples, which should not unduly limit the scope of the claims herein. One of ordinary skill in the art would recognize many other modifications, alternatives, and variations. As shown, the method begins at start, step 401. Here, the image scan includes a series of scans from right to left and back again, although these directions could be changed in the specific embodiment. When a line scan begins (step 403) a probe controller, which is coupled to the probe, sends (step 405) a voltage signal that is monitored (step 407) by a controlling computer and/or main controller. The voltage signal is often a pulse, which is sent from the probe controller at a beginning of each scan line from left to right and again on a return right to left line. If an image is to be constructed (step 409) of scans from left to right, the method detects the voltage pulse signaling the onset of scanning using computer software. The method sends a voltage signal to initiate illumination, step 411. Alternatively, if the image is not being constructed for the scan, the method returns via a branch back to step 405. The method also stops at step 413. Depending upon the embodiment, there can be many modifications, variations, and alternatives.

Referring to FIG. 5, the method includes using a modulator to turn-on and turn-off illumination of a feature of an object. As shown, the method begins at start, step 501. Here, the image scan includes a series of scans from right to left and back again, although these directions could be changed in the specific embodiment. When a line scan begins a probe controller, which is coupled to the probe, sends a voltage signal that is monitored by a controlling computer and/or main controller. The voltage signal is often a pulse, which is sent from the probe controller at a beginning of each scan line from left to right and again on a return right to left line. If an image is to be constructed of scans from left to right, the method detects (step 503) the voltage pulse signaling the onset of scanning using computer software. The method sends a voltage signal to initiate illumination. Alternatively, if the image is not being constructed for the scan, the method does not illuminate the feature of the object.

Preferably, the method includes transferring a control signal from the controller to a controller of an acousto-optic modulator. The control signal is used to drive (step 507) the modulator such that it switches the beam into the FANSOM optical system. The method continues to determine if the scan is finished, step 509. Depending upon the embodiment, the method can also monitor (step 515) the scan and whether illumination is desired during the scan. Alternatively, the method completes the scan and returns to step 503 for another scan, which may or may not drive the modulator to allow the beam into the FANSOM system. Preferably, when the return line scan begins, a second voltage pulse is generated by the probe controller. As the return line is not being used to create the image according to the preferred embodiment, the controller sends a voltage pulse (or no voltage pulse) to the modulator such that light no longer transmits into the FANSOM optical system and the feature of the object is not illuminated.

Depending upon the embodiment, the method repeats for each line with the feature of the object being illuminated only during left to right scans as the image is built up. Once the image is complete, the laser is commanded to switch off (also step 507) (in this case by stopping the voltage pulse to the modulator) until initiation of the next image scan. A triggering of each line scan can be actuated at the beginning of each line. Alternately it could begin based on topographical information from the probe (that is that the probe is over the sample of interest). Alternately the switching could be based on a user defined area or coordinate set. The switching itself can be accomplished in a variety of ways. These include using a shutter or chopper which is triggered or timed to correspond to the aforementioned inputs (beginning of line, coordinate, topographical information).

Depending upon the embodiment, there can be many benefits over conventional techniques. In a specific embodiment, the invention provides a capability to extend the lifetime of fluorescent molecules by turning the excitation laser on only during data gathering. Turning the laser off when the fluorescent molecules are not being imaged often ensures maximizes the life of the fluorescent molecule by preventing photobleaching. In addition this allows the signal to be maximized during imaging. Depending upon the embodiment, one or more of these benefits may be achieved. These and other benefits will be described in more throughout the present specification and more particularly below.

Although the above has been illustrated in terms of specific software and/or hardware features, it would be recognized that many variations, alternatives, and modifications can exist. For example, any of the hardware features can be further combined, or even separated. The features can also be implemented, in part, through software or a combination of hardware and software. The hardware and software can be further integrated or less integrated depending upon the application. Of course, one of ordinary skill in the art would recognize many other modifications, variations, and alternatives.

In an alternative specific embodiment, the invention provides a method for operating an apertureless microscope for viewing microscopic features of objects to molecular sensitivity. Conventional techniques have proved to be difficult in aligning laser sources with optical systems. Such difficulties have been overcome by way of the present method and system resulting therefrom. The method is provided as follows:

1. Couple a first assembly including a probe coupling a cantilever to an optical sub-system to facilitate spatial movement between the first assembly and the optical sub-system through a spatial translation axis;

2. Adjust the tip or the portion of the cantilever toward a test surface to focus the tip to a predetermined region of the test surface on the optical sub-system using the spatial translation axis;

3. Adjust a relationship between the alignment beam and the first assembly to an excitation laser such that the tip or the portion of the cantilever in the first assembly is within a vicinity of 1 micron of the excitation laser; and 4. Fine tune the excitation laser to align the tip or the portion of the cantilever using movement of the first assembly on the spatial translation axis.

The above sequence of steps provides a way to adjust a first assembly having a probe and cantilever to an optical sub-system, where the probe becomes aligned with the optical sub-system. Examples of such a probe and optical sub-system have been previously described herein, but can also be outside of the present specification. As can be seen, there is a general course alignment and fine alignment steps, and may also be others depending upon the application. Further details of the present method can be found throughout the specification and more particularly to the figures below.

Figure 6:
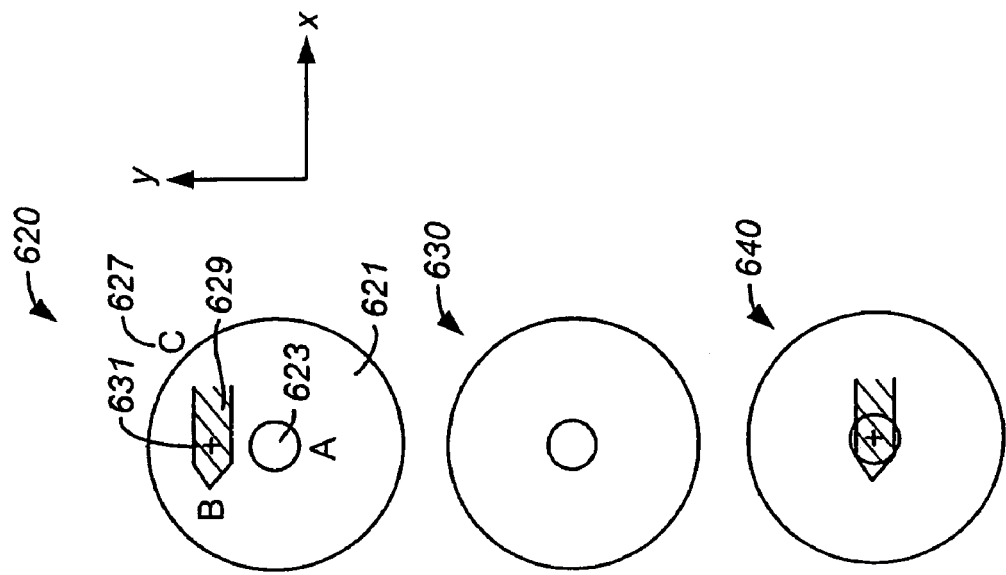
FIGS. 6 through 8 are simplified diagrams illustrating optical alignment methods for nanoscopic scanning according to embodiments of the present invention.
Figure 6:
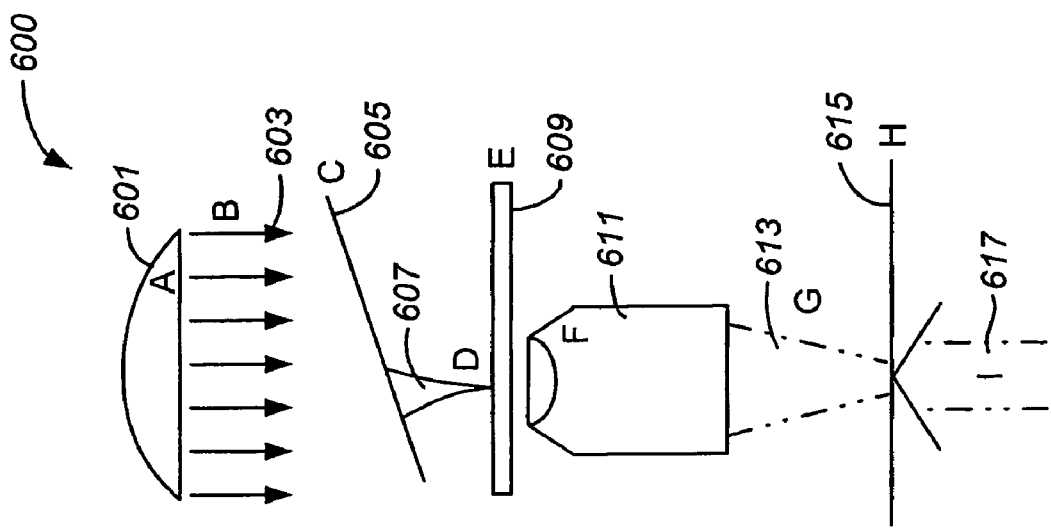
Figure 7:
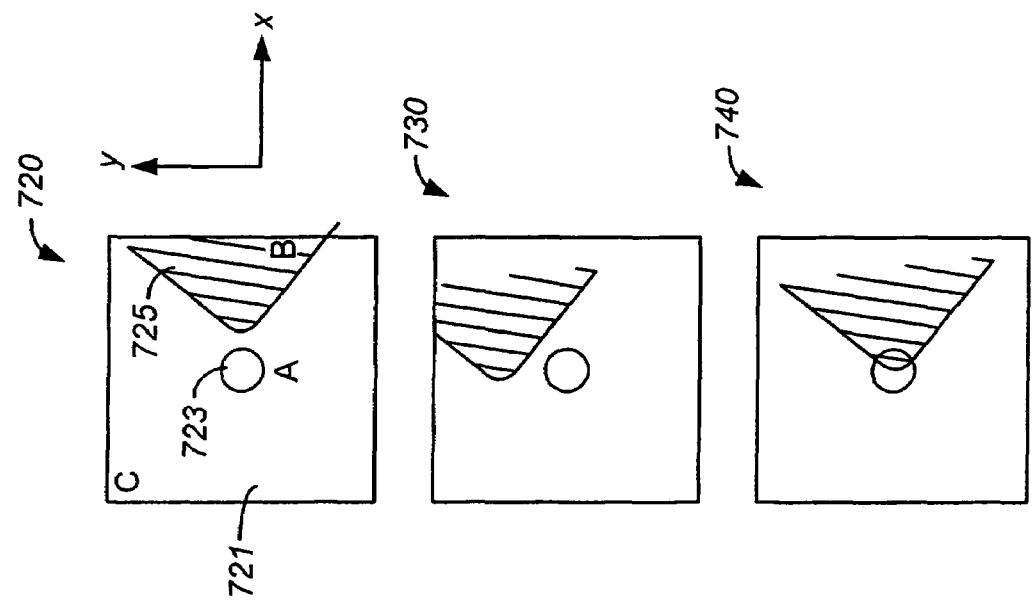
Figure 7:
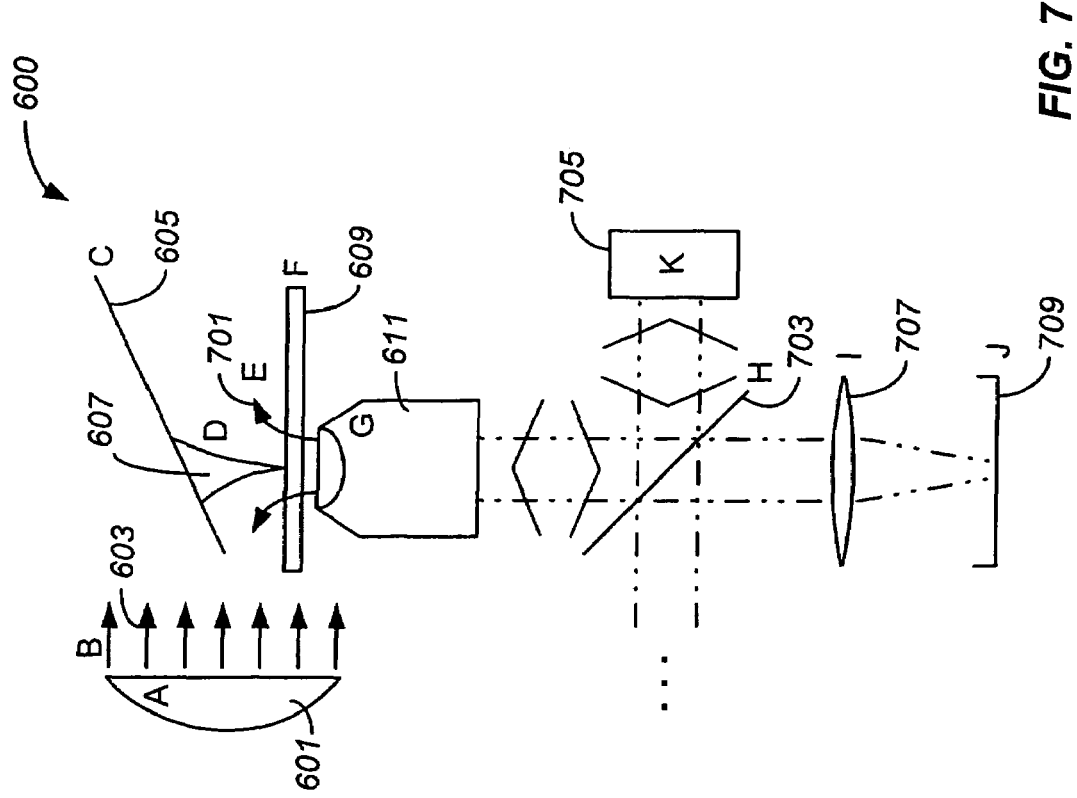
Figure 8:
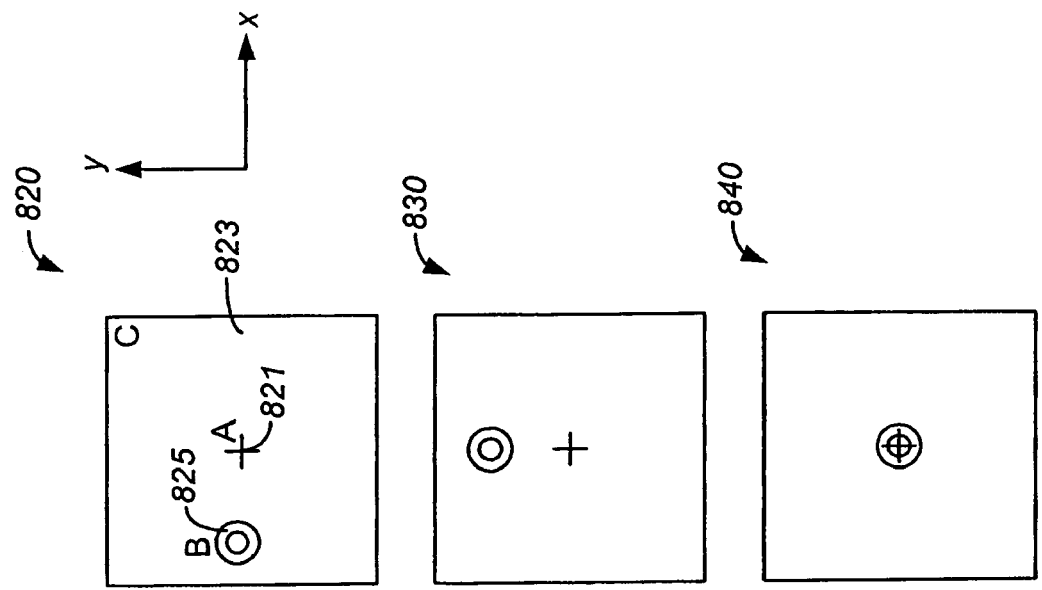
Figure 8:
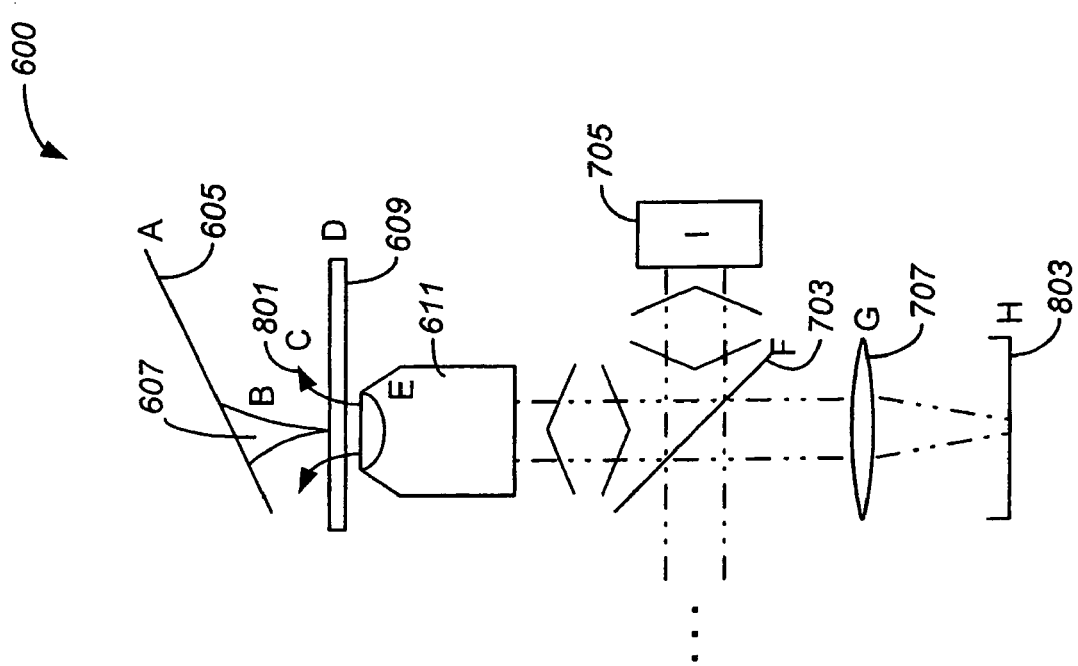
Figure 9:
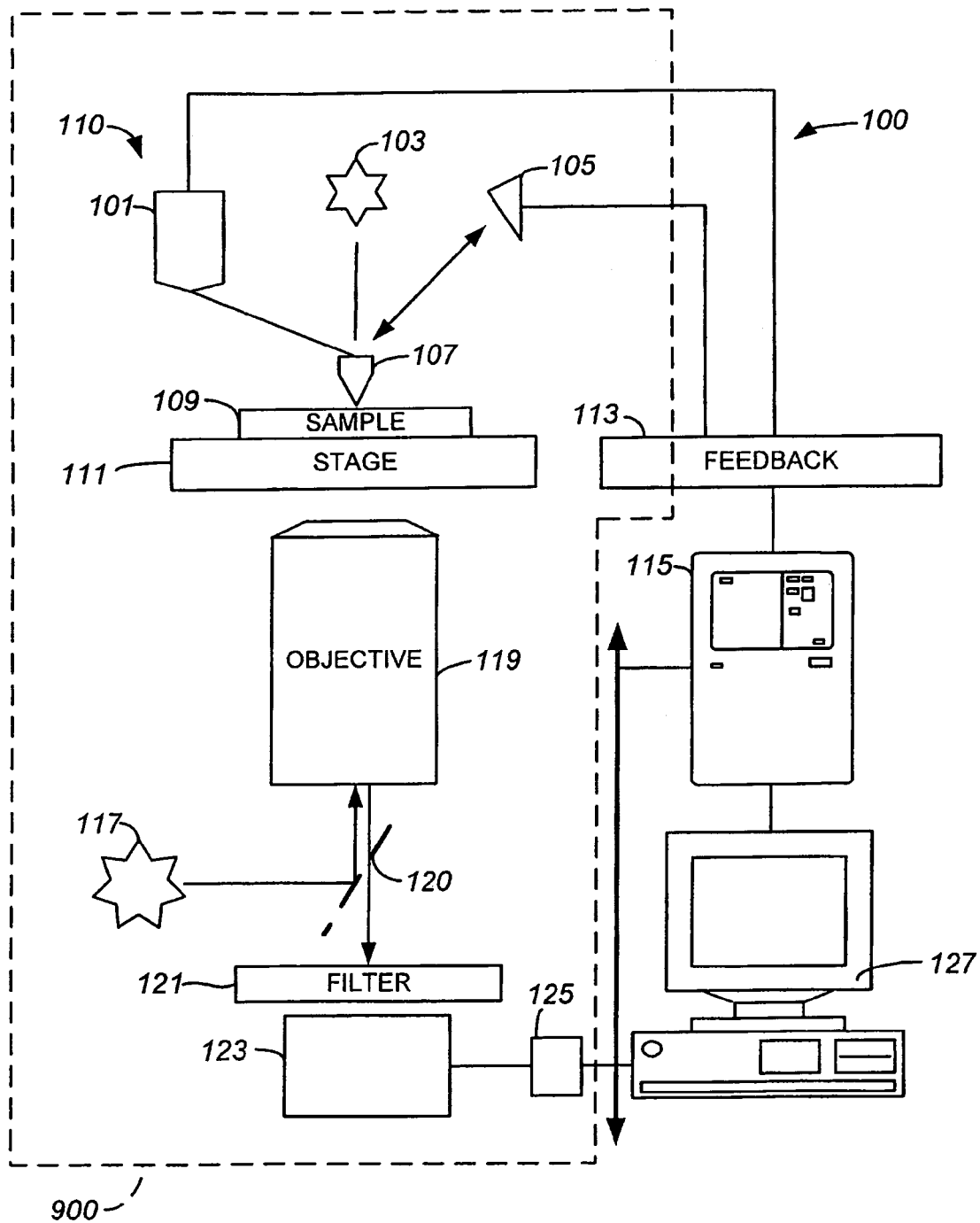
FIGS. 9 through 12 are simplified diagrams of packaging systems and methods for scanning systems according to embodiments of the present invention.

FIGS. 6 through 8 are simplified diagrams illustrating optical alignment methods for nanoscopic scanning according to embodiments of the present invention. As shown, the invention provides a method for operating an apertureless microscope for viewing microscopic features of objects to molecular sensitivity. The method includes aligning the excitation laser beam to a tip coupled to a cantilever through a probe or a portion of the cantilever within a first assembly. There are several methods for accomplishing such alignment to nanometric accuracy. Gross alignment within a few microns can be achieved by viewing the back reflection of the excitation laser beam and the cantilever laser illumination of the cantilever and either moving the cantilever assembly until the two beams are properly aligned. Alternately or in combination a tip-tilt mirror can be used to move the focus of the excitation laser so that it is properly aligned with the cantilever tip. Additionally, the shadow cast by the cantilever when illuminated by the excitation laser can be visualized or imaged and used to align the tip with the excitation laser.

Referring to FIG. 6, illustrated is a simplified system diagram 600 including a lamp 601, which outputs white light 603. A cantilever 609 is coupled to prove tip 607. The probe tip is faced toward cover slip 609, which also may be a plane of a sample. A microscope objective 611 is coupled to the probe. The system also has shadow formation region 613, which is projected to screen 615, which may be temporary and/or removable. The system also has excitation laser source 617 which projects onto the backside of the screen. The excitation laser source which projects through the objective. Other features of the present system have been previously described above, but can also be found throughout this specification.

The method performs a gross alignment step, which aligns the laser, which is on a lower subsystem to the probe tip, which is on an AFM subsystem or assembly. As shown, reference numeral 620 illustrates a projection on the screen, which is transparent in nature. Laser spot is illustrated by reference numeral 623. The projection also includes a shadow of cantilever 629 and perimeter of field of view 627. The probe tip, which is coupled to a larger assembly, is adjusted relative to the laser spot. A mis-aligned cantilever along the positive y-axis is shown by reference numeral 620. A mis-aligned cantilever along the x-axis is shown by reference numeral 630. An aligned cantilever and laser spot are provided in the illustration of reference numeral 640. Such aligned cantilever aligns the probe to the laser, which is coupled to the lower optical system.

In a specific embodiment, the method performs another alignment step, which aligns the laser to the probe in a finer manner. Such fine alignment to approximately 1 micron can be achieved by illuminating the cantilever either with monochromatic light or broadband light such that the optics can image the cantilever tip shadow relative to the excitation laser. Piezoelectric actuators can be used to either move the tip until properly aligned with the excitation laser or to steer the excitation laser until it is properly aligned with the tip. Alignment is achieved by way of an optical subsystem, which can be viewed using a display coupled to an image capturing camera or the like.

FIG. 7 is a simplified system diagram 600 including image capturing device which is coupled to a display device. Like reference numerals are used in this diagram as the prior diagram merely for illustration. The system includes lamp 601, which outputs white light 603. The cantilever 609 is coupled to prove tip 607. The probe tip is faced toward cover slip 609, which also may be a plane of a sample. The microscope objective 611 is coupled to the probe. The system also has photons from the excitation laser diverging from the objective 611. The system has dichroic mirror 703, which directs radiation from laser 705 through the objective. An image captured from the probe via white light traverse through eyepiece lens 707 from objective and through mirror. Such white light is captured via image capturing device 709, which is a CCD camera or the like. Other features of the present system have been previously described above, but can also be found throughout this specification.

A relationship between the probe tip and laser beam is illustrated by reference numerals 720, 730, and 740. As shown, a display 721 is coupled to the camera, which captures the white light images. The display illustrates laser spot 723 and probe tip 725. Reference numeral 720 illustrates a mis-aligned probe tip along an x-axis direction from the beam. Reference numeral 730 illustrates a y-direction mis-alignment. An aligned probe tip and laser beam are illustrated by way of reference numeral 740. Such alignment provides the finer alignment according to an embodiment of the present invention. By way of example only, the relationship between the probe and the laser is adjusted by way of an automated x-y-z state, which has automated and/or semi-automatic control features according to a specific embodiment.

The method also performs a fine alignment between the probe and the laser beam according to preferred embodiments. Referring to FIG. 8, illustrated is a system including a raster image using an avalanche photo diode or the like. Like reference numerals are used in this diagram as the prior diagram merely for illustration. The system includes cantilever 609 coupled to prove tip 607. The probe tip is faced toward cover slip 609, which also may be a plane of a sample. The microscope objective 611 is coupled to the probe. The system also has photons from the excitation laser diverging from the objective 611. The system has dichroic mirror 703, which directs radiation from laser 705 through the objective which is backscattered from the probe tip. Back scattered light from the probe traverse through eyepiece lens 707 from objective and through mirror. Such backscattered light is captured via avalanche photo diode 803. Other features of the present system have been previously described above, but can also be found throughout this specification.

A relationship between the probe tip and laser beam is illustrated by reference numerals 820, 830, and 840. As shown, a display 823 is coupled to the avalanche photodiode, which captures the backscatter images. The display illustrates laser spot 825 backscatter and a center 821 of a raster field of view, which is the alignment point. Reference numeral 820 illustrates a mis-aligned probe tip along an x-axis direction from the beam. Reference numeral 830 illustrates a y-direction mis-alignment. An aligned probe tip and laser beam via raster field of view are illustrated by way of reference numeral 840. Such alignment provides the finer alignment according to an embodiment of the present invention. By way of example only, the relationship between the probe and the laser is adjusted by way of an automated x-y-z state, which has automated and/or semiautomated control features according to a specific embodiment.

As noted, the method includes fine and ultrafine alignment to as little as a few nanometers. Such alignment can be achieved by imaging the backscatter of the excitation laser either when scanning the laser over the cantilever tip or alternately when scanning the tip over a fixed focus excitation laser. The backscatter image gives a high resolution image via the microscope objective which allows the relative positions of the tip and the laser to be established. Final alignment can then be achieved by either moving the cantilever assembly, moving the cantilever tip or the excitation laser focus point until the excitation laser and the cantilever tip are properly aligned. All of the previously mentioned alignment steps can be carried out separately or in combination. Also they can be carried out in combination with a properly marked sample substrate which incorporates appropriate position reference points and or structures. Alignment can be maintained while imaging in several ways. It can be achieved by imaging the excitation laser back reflection. The imaged diffraction pattern can then be used to monitor changes in relative position which can be used to correct any misalignments which develop if the laser tracks the cantilever tip while imaging a sample. Alternately, information associated with the pattern can be used to provide primary commands to move the excitation laser to track a moving cantilever tip. Finally it can be used to correct other accumulated misalignments including but not limited to thermal drift and strain relaxation, hysteresis, and piezo creep. These techniques can be used to achieve and maintain alignment whether the cantilever tip scans a stationary sample and excitation laser, both the cantilever tip and excitation laser scan a stationary sample, the excitation laser scans a stationary cantilever tip and sample, or a stationary cantilever tip and excitation laser scan a moving sample.

Although the above has been illustrated in terms of specific hardware and/or software features, it would be recognized that many variations, alternatives, and modifications can exist. For example, any of the hardware features can be further combined, or even separated. The features can also be implemented, in part, through software or a combination of hardware and software. The hardware and software can be further integrated or less integrated depending upon the application. One of ordinary skill in the art would recognize many alternatives, variations, and modifications.

FIGS. 9 through 12 are simplified diagrams of packaging systems 900 and methods 1200 for scanning systems according to embodiments of the present invention. These diagrams are merely examples, which should not unduly limit the scope of the claims herein. One of ordinary skill in the art would recognize many other variations, modifications, and alternatives. As shown, the system includes a package 900 to protect an environment of sensitive scanning and measurement equipment. Preferably, the scanning system is an apertureless microscope system for viewing one or more features of samples to a resolution of molecular sensitivity. The system maintains a controlled environment for elements including sample 109 coupled to stage 111. The elements also include AFM probe 107, which is coupled to drive 101, through cantilever member. Source 103 and detector 105 are also enclosed in the environment. Other elements include objective 119 coupled to mirror 120 and laser source 117. Filter 121 is coupled to sensor 123 and is coupled to detector 125. Each of these elements are also included in the controlled environment. Of course, some of these elements may be removed while others added without departing from the scope of the claims herein. Preferably, at least the AFM probe 107, sample 109, stage 111 and objective 119 are included in the controlled environment.

The controlled environment allows for accurate measurement of one or more features on a sample. Depending upon the embodiment, the controlled environment has a predetermined temperature, lighting, pressure, gas mixture, any combination of these, and the like. The environment can also be free from contaminants, e.g., organic, inorganic. Preferably, the environment is free from coupled mechanical vibration, i.e., equivalent to less than 1% of an output signal of measurement, although others may work as well. Other embodiments may require an oxygen rich environment. Still others may include a non-reactive environment, which is rich with nitrogen bearing particles and/or non-reactive noble gases, any combination of these, and the like. In many cases, the sample may be maintained and imaged in a biologically relevant fluid environment. Of course, the environment depends highly upon the particular application.

Figure 10:
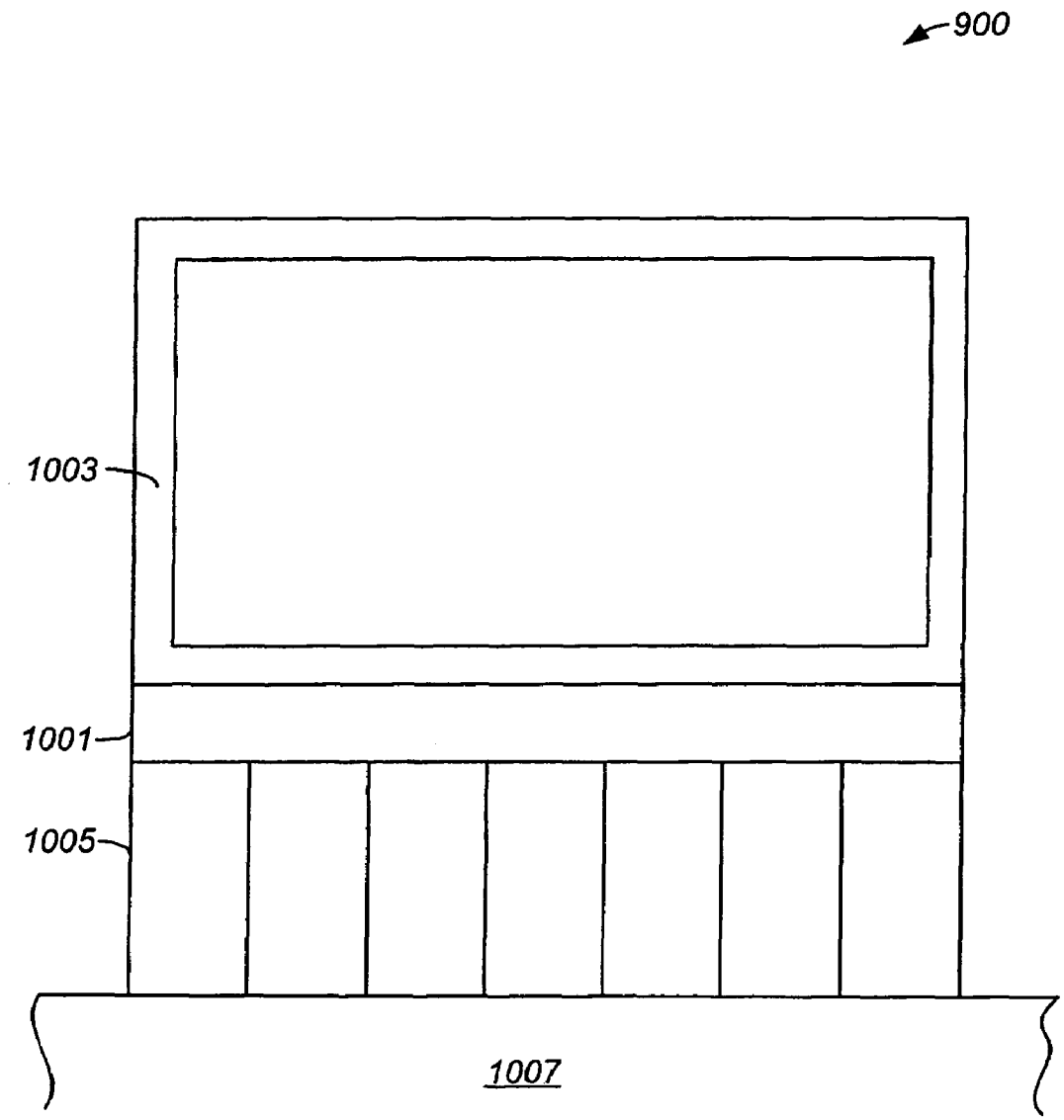
Figure 11:
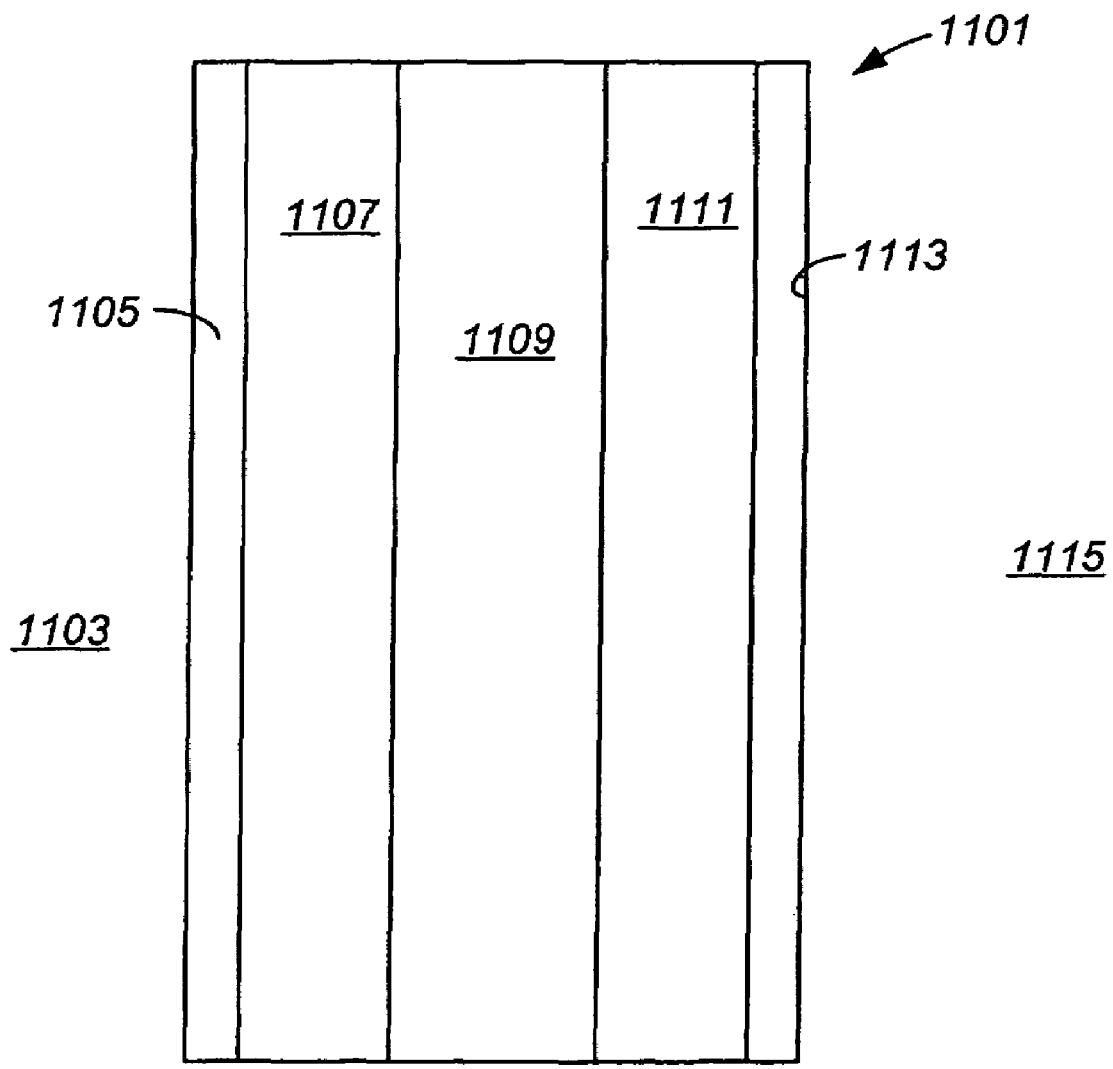

Referring to FIG. 10, the controlled environment is provided using system 900. The system has a member 1007 for supporting the apertureless microscope system. A support structure 1001 is coupled to the member to support the member. A plurality of shock absorbing devices 1005 is coupling the support structure and the member. The plurality of shock absorbing devices is capable of substantially eliminating a possibility of mechanical noise from the floor structure. Preferably, the shock absorbing device is a sorbothane manufactured by Sorbothane corp., but can also be others. The shock absorbing device has a suitable length and capable of supporting 2 or more pounds. At least all vibration sensitive elements, and vibration producing elements (e.g. those with fans are included. Preferably, the shock absorbing devices substantially eliminate high frequency (e.g., >10 Hz) noise from entering the controlled environment through the floor structure.

The system also has an enclosure structure 1003 coupled to the member and covering the apertureless microscope system. The enclosure houses the apertureless microscope within an opening confined within the enclosure structure. The enclosure can be made of a suitable material that is rigid and can maintain the environment. Preferably, the enclosure is made of a plastic, a metal, or wood, as well as any combination of these. As merely an example, the enclosure is made of wood, but can also be made of other materials. A cross-sectional-view of the enclosure has been provided by FIG. 11, which is not intended to be limiting.

As shown, the cross-sectional view includes an outer region exposed to an outer environment 1103 and an inner region exposed to the controlled environment 1115. The outer environment is often a laboratory or other location where human beings often work. The controlled environment is a region occupied by the scanning system, as previously noted. The enclosure includes rigid structure 1109. As noted, the rigid structure can be made of a suitable material for supporting the enclosure and overlying materials. The enclosure may also include a frame to support the rigid structure or semi-rigid structure. Such frame can also include walls according to specific embodiments. A sound absorbing member 1111 is coupled to the enclosure structure to substantially eliminate a possibility of acoustic noise from entering into the opening from an external source within the enclosure structure. Preferably, the sound absorbing member is a foam composite, but can also be other sound deadening materials. An inner liner 1107 is also coupled within the opening of the enclosure structure to absorb one or more stray photons within the enclosure structure. The inner liner is generally capable of substantially preventing the stray photons from being released back into the enclosure structure. As an example, the inner liner is a composite manufactured by EAR Composites Inc. A reflective member (e.g., aluminum or other metal, or aluminized mylar or dense plastic) 1105, 1113 can be formed overlying outer surfaces of the enclosure structure. The outer reflective member is configured to substantially eliminate a desired acoustic noise from entering into the opening within the enclosure structure by reflecting a desired acoustic noise on the reflective surface. Depending upon the embodiment, there can be other layers, which are interposed between any pair of layers described. Some of these layers may be sound absorbing or serve to support the reflective layers. Other embodiments may remove one or more of the layers. Additionally, each layer can be a single material, a composite, or multi-layered, depending upon the embodiment.

Although the above has been illustrated in terms of specific hardware features, it would be recognized that many variations, alternatives, and modifications can exist. For example, any of the hardware features can be further combined, or even separated. Further details of the functionality of the present invention can be outlined below.

According to the present invention, a method for operating a scanning system in a substantially noise free environment is provided as follows.

1. Insert a sample having a molecular feature on a stage of an apertureless microscope system, which has at least a scanning apparatus including a probe coupled to an optical imaging apparatus;

2. Capture information having a feature size of less than five nanometers from a portion of the sample;

3. Maintain at least the stage and the sample in an opening confined by an enclosure structure, which is coupled to a member for supporting a portion of the apertureless microscope system;

4. Maintain at least the stage and the sample free from mechanical vibration noise using a plurality of shock absorbing devices coupling the member, where the plurality of shock absorbing devices is capable of substantially eliminating a possibility of mechanical vibration noise from an external source;

5. Maintain at least the stage and the sample free from acoustic noise using a sound absorbing member coupled to the enclosure structure to substantially eliminate a possibility of the acoustic noise from interacting with the captured information; and 6. Capture one or more stray photons within the opening of the enclosure structure using an inner liner coupled within the enclosure structure to absorb the one or more stray photons within the enclosure structure.

The above sequence of steps is used to perform a method for operating a scanning system in a substantially noise free environment for viewing one or more features of a sample(s) to a resolution of molecular sensitivity. The method allows users of the scanning system to work around it without substantial interference of measurements derived from the system. Further details of the present method are provided throughout the present specification and more particularly below.

Figure 12:
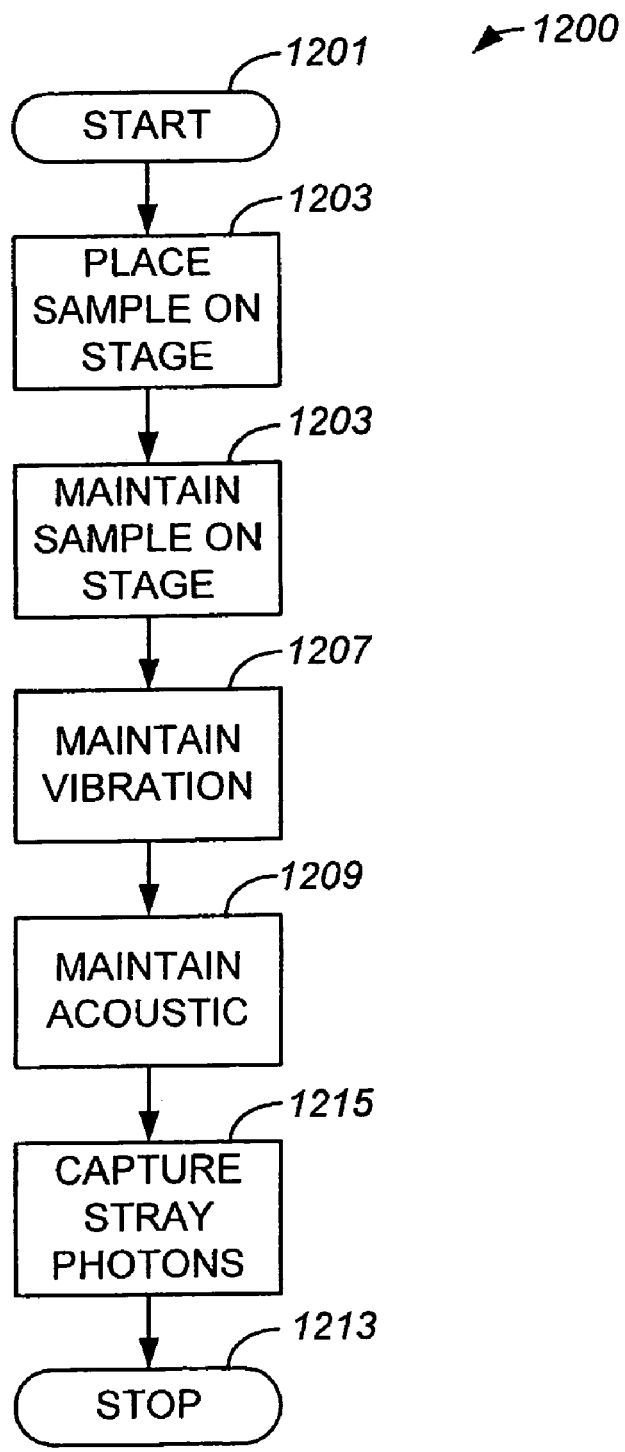
Figure 13:
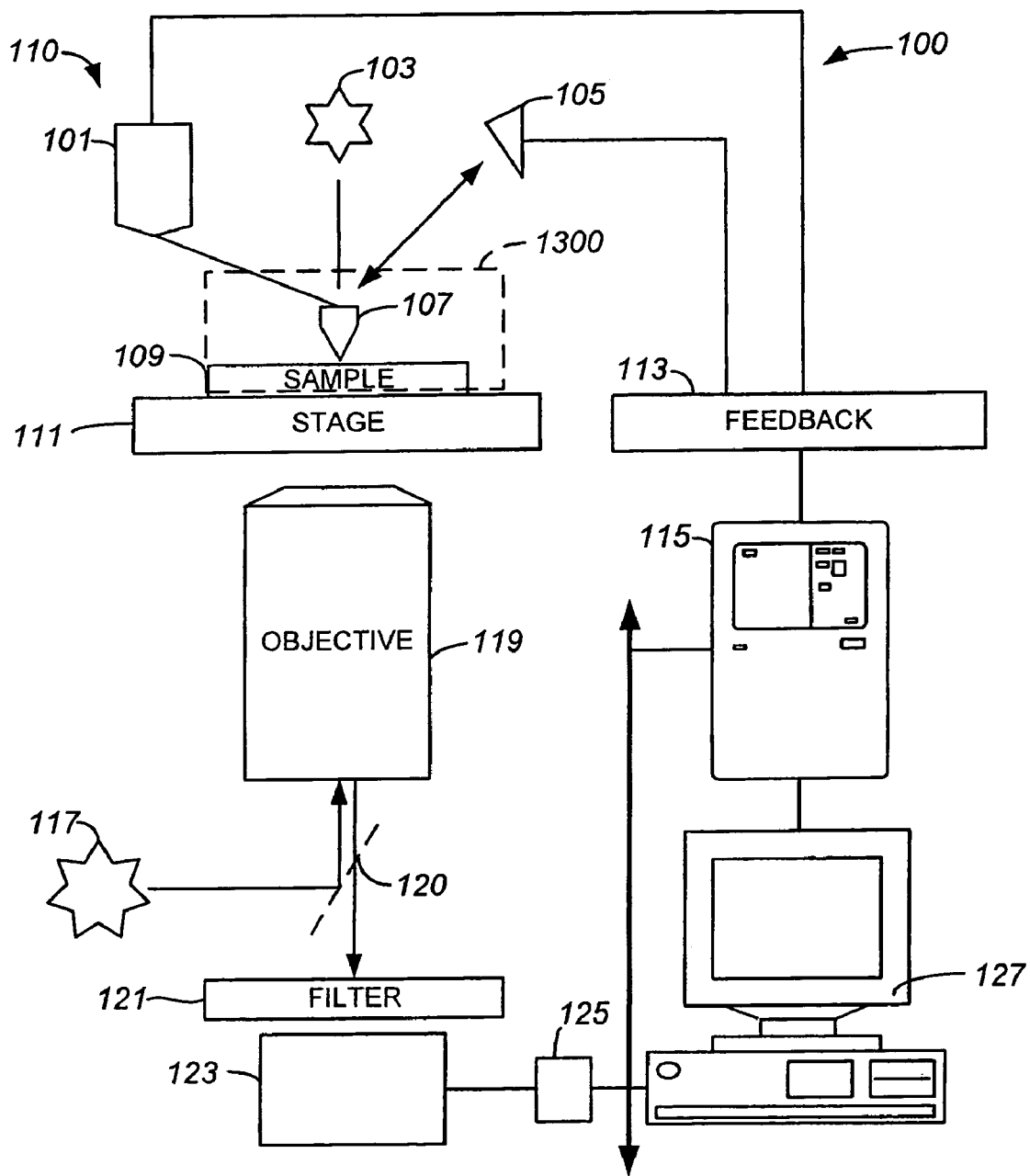
FIGS. 13 through 16 are simplified diagrams of various tip devices according to embodiments of the present invention.

Referring to FIG. 12, the method 1200 begins with start, step 1201. The method includes inserting (step 1203) a sample having a molecular feature on a stage of an apertureless microscope system, which has at least a scanning apparatus including a probe coupled to an optical imaging apparatus. An example of such an apparatus has been described above, but can also be outside of this specification according to certain embodiments. Alternatively, the apparatus can be sample scanning with fixed optics and probe, probe scanning with fixed sample and optics, optically scanned with fixed sample and probe, and probe and optically scanned with fixed sample. The optical imaging apparatus is adapted to capture information having a feature size of less than five nanometers from a portion of the sample in preferred embodiments.

Once the sample has been placed on the stage, the method maintains a controlled environment. In a specific embodiment, the method maintains (step 1203) at least the stage and the sample in an opening confined by an enclosure structure. Preferably, the enclosure structure is coupled to a member for supporting a portion of the apertureless microscope system. The method maintains at least the stage and the sample free from mechanical vibration noise (step 1207) using a plurality of shock absorbing devices coupling the member. The plurality of shock absorbing devices is capable of substantially eliminating a possibility of mechanical vibration noise from an external source. Other techniques could also be used, as well.

The method further maintains at least the stage and the sample free from acoustic noise (step 1209) using a sound absorbing member. Preferably, the sound absorbing member is coupled to the enclosure structure to substantially eliminate a possibility of the acoustic noise from interacting with the captured information. An example of such a sound absorbing member has been provided. The method then has a step of capturing (step 1215) one or more stray photons within the opening of the enclosure structure using an inner liner. Such inner liner is coupled within the enclosure structure to absorb the one or more stray photons within the enclosure structure. The inner liner is capable of substantially preventing the one or more stray photons from being released back into the opening of the enclosure structure. Depending upon the embodiment, there may be other steps that are included and/or possibly removed.

Although the above has been illustrated in terms of specific hardware and/or software features, it would be recognized that many variations, alternatives, and modifications can exist. For example, any of the hardware features can be further combined, or even separated. The features can also be implemented, in part, through software or a combination of hardware and software. The hardware and software can be further integrated or less integrated depending upon the application. One of ordinary skill in the art would recognize many alternatives, variations, and modifications.

Figure 14:
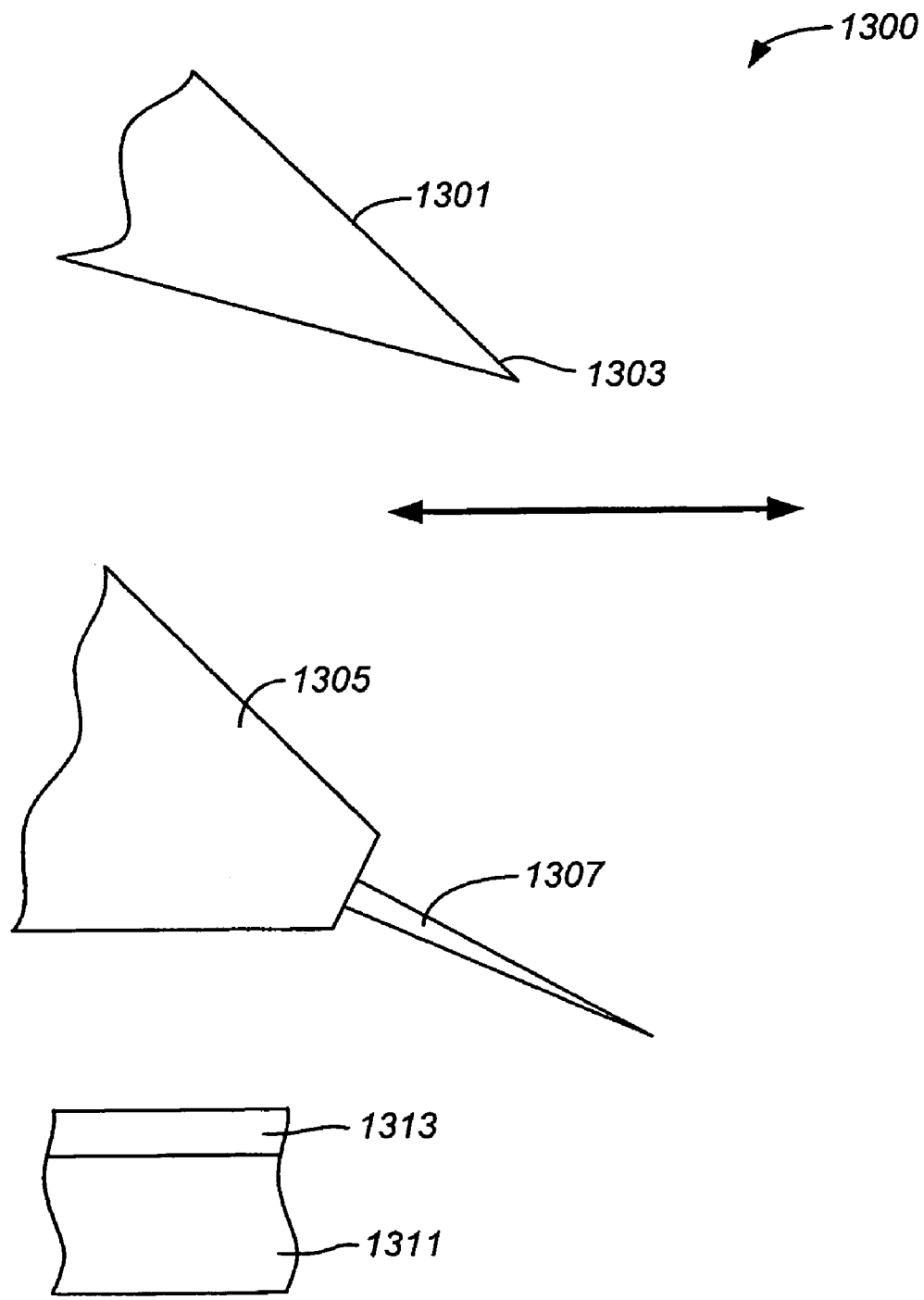

FIGS. 13 through 16 are simplified diagrams of various tip devices according to embodiments of the present invention. These diagrams are merely examples, which should not unduly limit the scope of the claims herein. One of ordinary skill in the art would recognize many other variations, modifications, and alternatives. As shown, the system includes common elements as the prior figures without unduly limiting the scope of the claims herein. The present tip devices are provided within the region surround by the dotted line and indicated by reference numeral 1300. As shown, the tip 107 is coupled to a cantilever, which is coupled to a drive device. Preferably, the tip is a nanotube based structure, but can also be like structures, depending upon the embodiment. Referring to FIG. 14, the nanotube structures 1300 include at least a pyramid shaped structure 1301, which includes tip 1301. Additionally, such structures include a multi-diameter structure 1305, which includes tip 1307. The nanotube structure can be single walled, multi-walled, or any combination of these. Preferably, the nanotube structure is single walled and made of pure or doped carbon. Alternately the nanotube could be made of doped carbon. As merely an example, such single walled structure is a PIT tip from a company called Nanosensors of Germany, but can also be others (for example AC240TM tips from Olympus of Japan). In certain embodiments, the nanotube structure 1311 is coated with an overlying layer 1313. Here, the nanotube structure can be a semiconductor or conductor. The overlying layer or layers (if multilayered) is a conductor, e.g., metal. The metal's used include platinum, gold, silver alloys, aluminum, platinum-iridium, cobalt and many others. Preferably, the metal is high purity gold or platinum. The nanotube structure can also include a length of less than 250 nanometers in certain embodiments, but will generally have a range of length, e.g., 5-100 nanometers, 10-30 nanometers, depending upon the application.

Figure 14A:
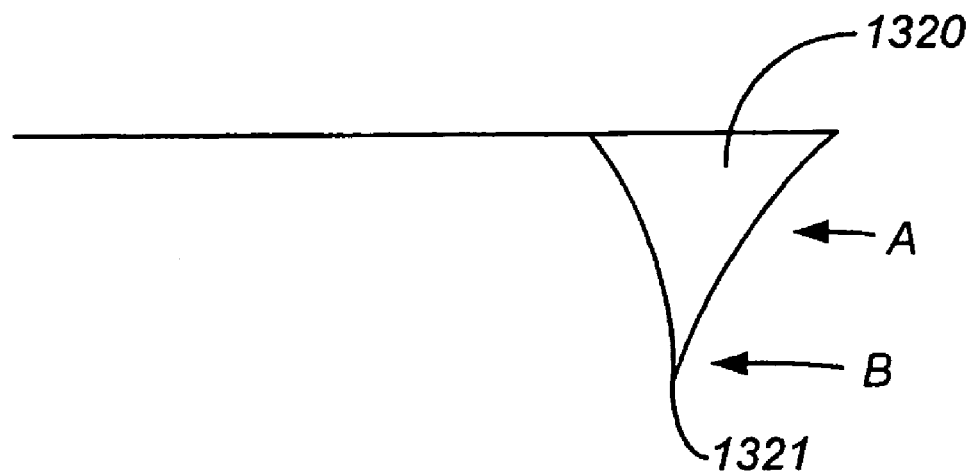
FIGS. 14A and 14B are nanotube based probes according to embodiments of the present invention.
Figure 14B:
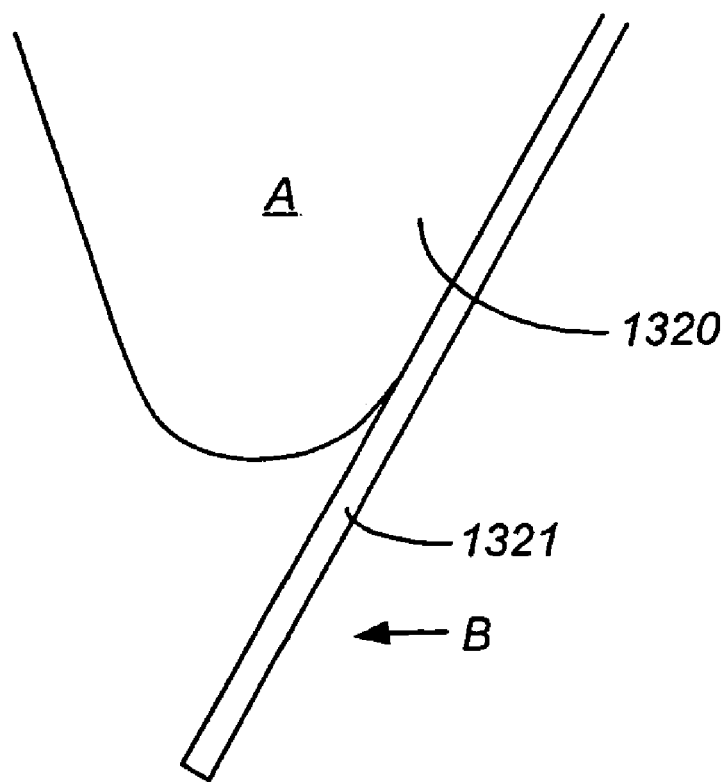

The metal is deposited using a deposition process. Such deposition process includes evaporation, chemical vapor deposition, sputtering, or molecular beam epitaxy. Preferably, the deposition process is molecular beam epitaxy, which forms a high quality layer of single crystal metal. The thickness of such metal is preferably less than 3 nm, although other thicknesses can be used. The combination of nanotube structure and overlying layer is less than 5 nm diameter near a tip region in preferred embodiments. This compares with commercially available metalized AFM probe diameters of 30 nm from Olympus of Japan. The coated nanotube structures should enhance coupling with an excitation laser light according to certain embodiments. Alternative embodiments are provided by the simplified diagrams of FIGS. 14A and 14 B, which are nanotube based probes. Such probes include AFM probe 1320 coupled to nanotube probe 1321. Depending upon the application, there can be many other variations, modifications, and alternatives.

According to an alternative embodiment, metal coating is used for one or more sides of a DNA molecule. Such coated DNA molecule is attached to the probe such that it provides higher resolution images while still modulating the optical signal from the sample being imaged. A DNA molecule coated with gold on one side can have a typical diameter of less than 8 nm.

Figure 14C:
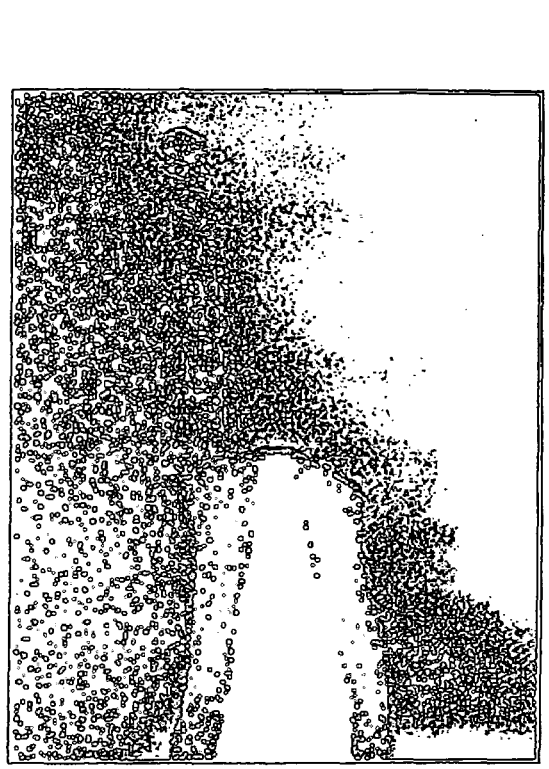
FIGS. 14C through 14E are nanotube based probes according to alternative embodiments of the present invention.
Figure 14D:
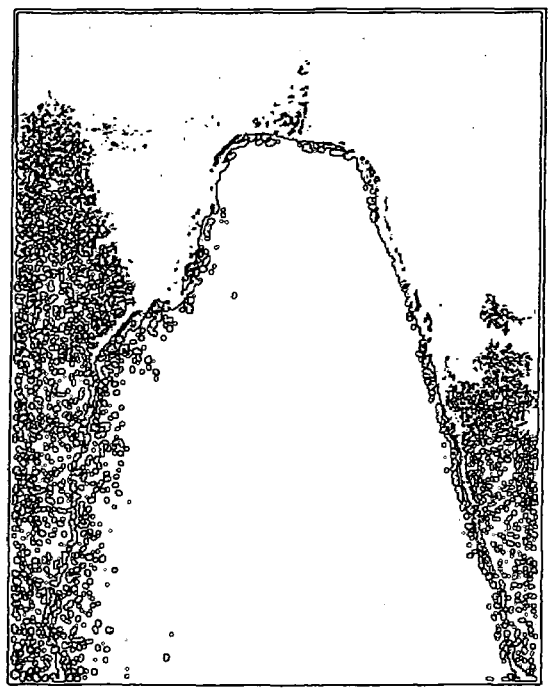
Figure 14E:
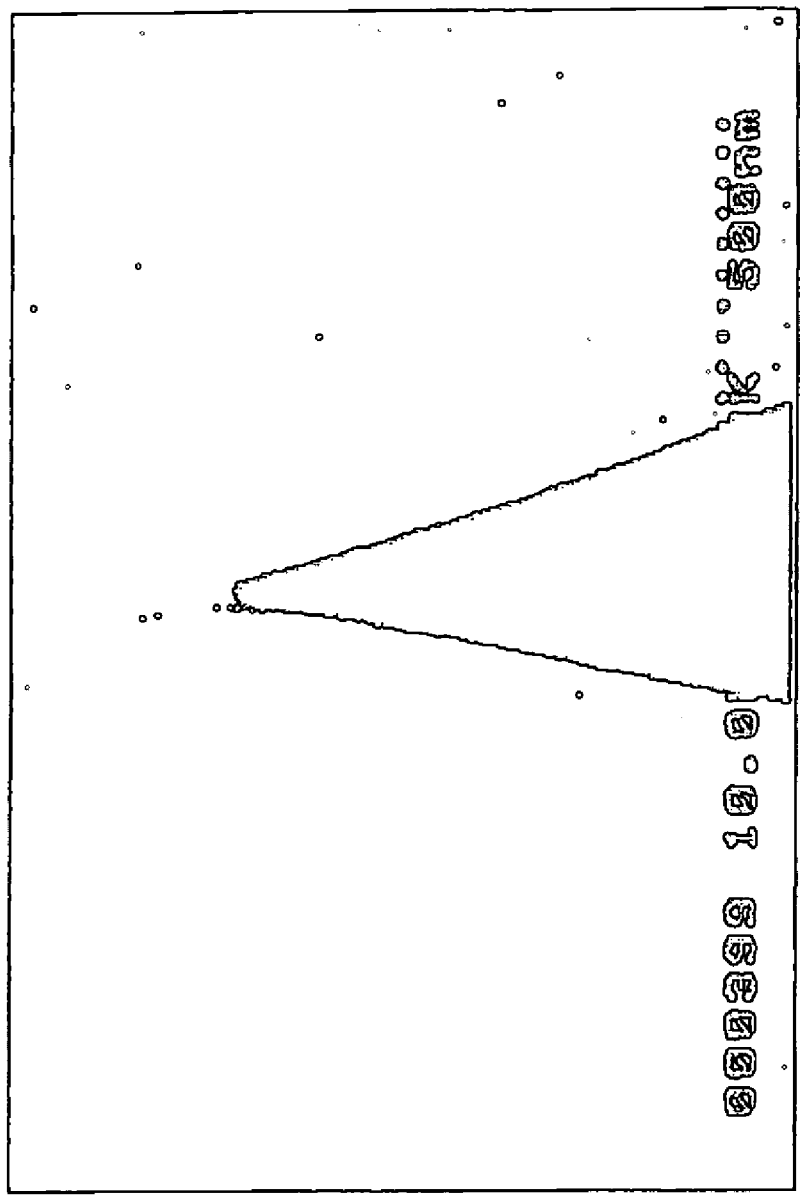

Other alternative embodiments are illustrated by the photographs 1401, 1403, 1405 of FIGS. 14C, D, and E. Referring to FIGS. 14C and D, TEM images of shortened nanotube ropes attached by pickup are shown. As shown, nanotube rope dimensions on the right side axis and are approximately 8 nm in width by 62 nm in length. The nanotube tip on the left is approximately 12 nm long and 5 nm in diameter. Referring to FIG. 14E, scanning electron micrographs of an individual, unshortened carbon nanotube mounted on silicon AFM probe is illustrated. The nanotube was picked up from a flat substrate supporting SWNTs grown by metal catalyzed chemical vapor deposition. Of course, there would be many other alternatives, variations, and modifications.

Figure 15:
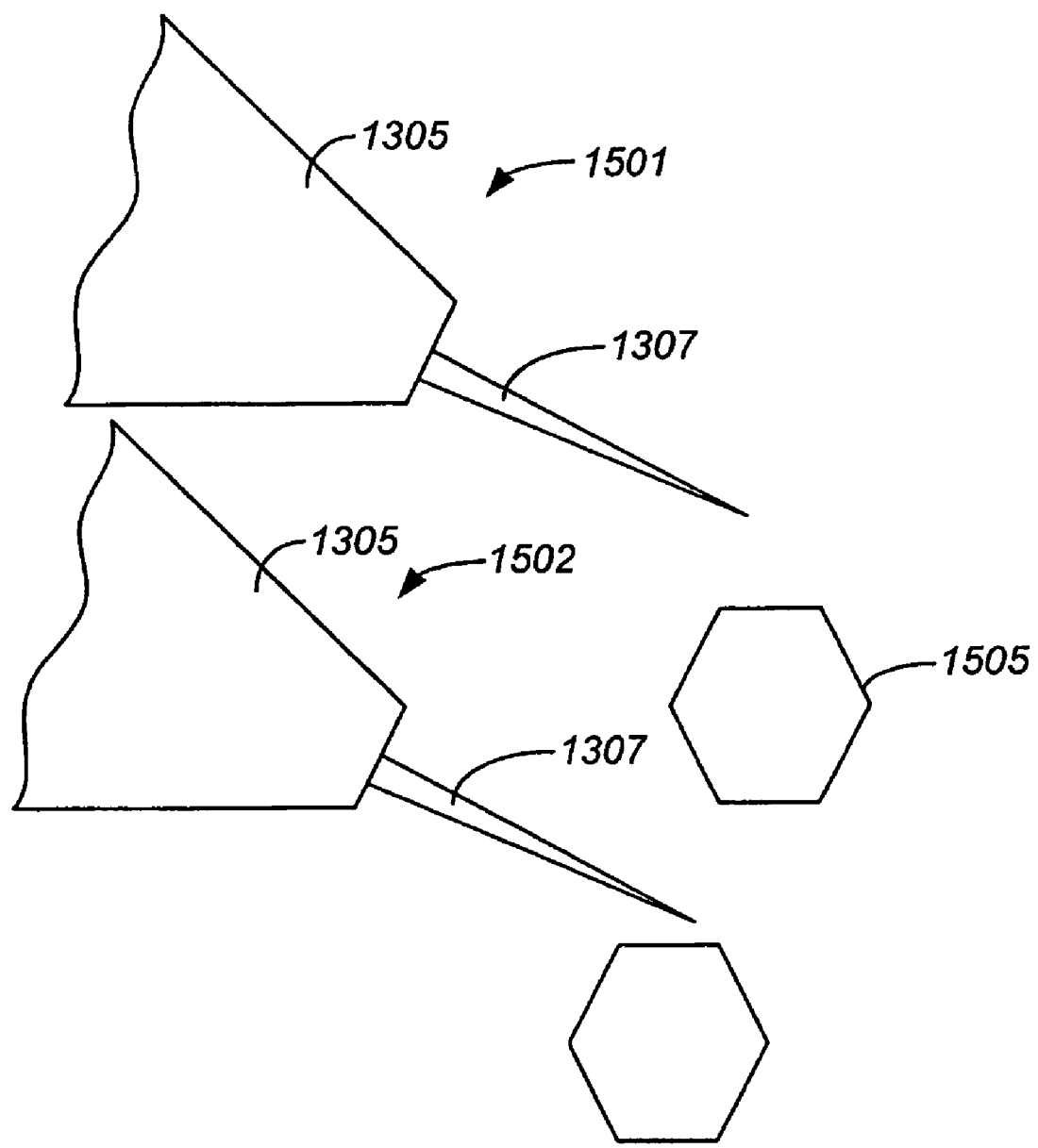
Figure 16:
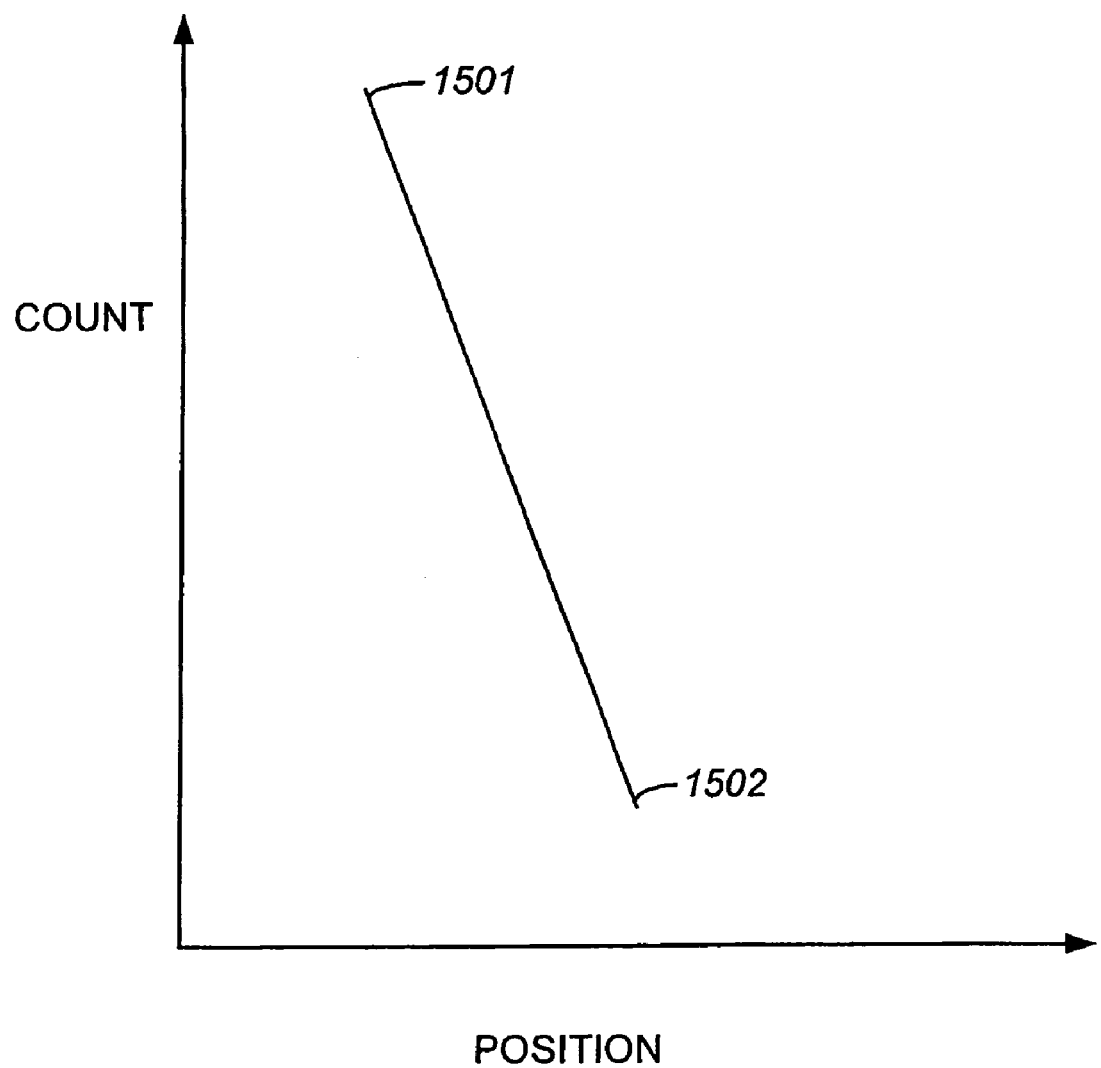

In a specific embodiment, a method for using the coated nanotube probe can be illustrated by way of FIG. 15. As shown, the nanotube probe includes a first state 1501 and a second state 1502. A sample 1505 is also included. The first state has the probe above the sample while the second state is on or in a vicinity of the surface of the sample as shown. As merely an example, an output detected by the present system is shown in the simplified plot of FIG. 16. The plot includes vertical axis, which is photon count, along probe position. Further details of such plot are provided throughout the specification and more particularly below.

Although certain figures have been described in terms of a specific nanotube structure, one of ordinary skill in the art would recognize many variations, alternatives, and modifications. For example, the nanotube material can be made of homogeneous material, a composite, or even a coated structure. The coating may be a metal, as noted. The metal can include a conductive metal such as platinum, gold, silver, cobalt, and various alloys of such metals such as platinum iridium alloy and the like. Of course, there can a variety of variations without departing from the scope of the claims herein.

Experimental Results:

To prove the principle and operation of the present invention, we performed experiments. The present invention used the FANSOM system, which has been previously described. Such FANSOM used a Digital Instruments BioScope AFM, which had a controller. The controller was a NanoScope IIIa, also manufactured by Digital Instruments of Santa Barbara, Calif. A second closed-loop BioScope AFM has also been used with a NanoScope IV controller. The microscope objective is a 1.3 NA 100× oil immersion objective, which was manufactured by Olympus of Japan.

The system used a PIT tip with platinum and iridium manufactured by NanoSensors of Germany. Such tip had a 75 kHz. The samples prepared 20 nanometer (nm) latex beads from a company called Interfacial Dynamics of Portland, Oreg. Such beads were coated with a fluorescent dye, e.g., Nile Red 2 dye. The experiments were performed in room temperature at atmospheric pressure. Although these parameters have been used, there can be many other variations, modifications, and alternatives.

Figure 17:
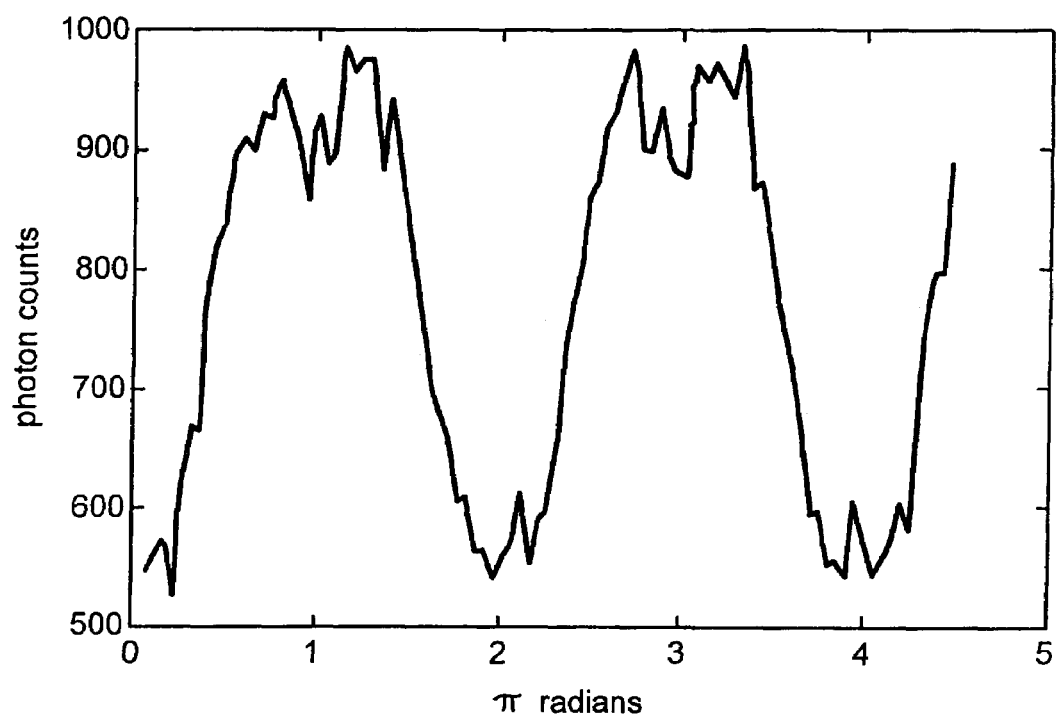
FIGS. 17 through 21 are experimental results using selected tip designs according to embodiments of the present invention.

Using the experiment, we demonstrated the probe. Referring to FIG. 17, as the probe came within a vicinity of a surface of the sample, photon counts decreased. As merely an example, the high photon count corresponded to a 120 nanometer distance between the surface of the sample and the probe. The lower photon counts corresponded to contact between the probe and the sample. As shown, a rate of fluorescence is shown modulated as the cantilever tip oscillates above the sample.

Figure 18:
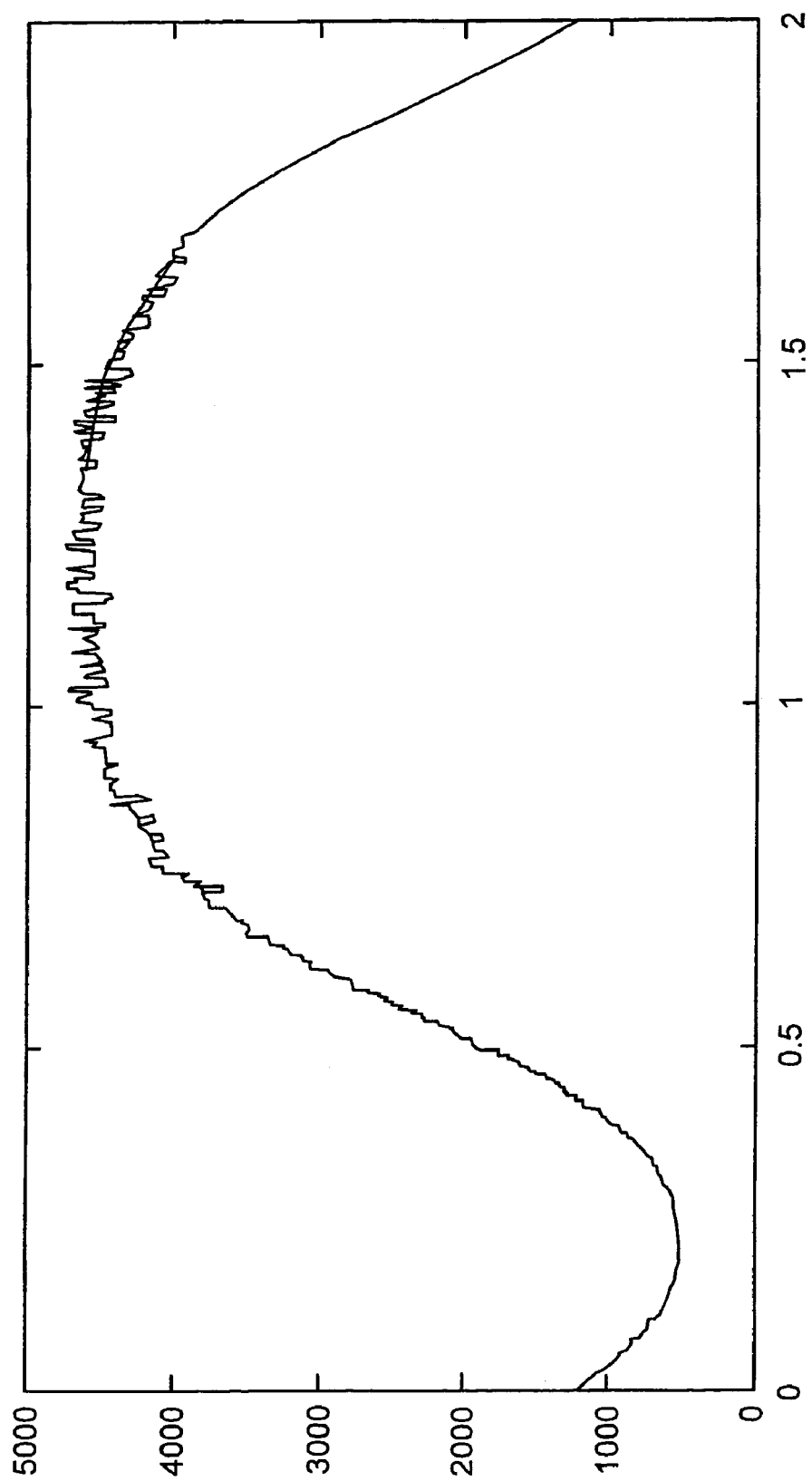

Another example of our experiment is provided by the simplified diagram of FIG. 18. As shown, a number of photons (y-axis) emitted by a 20 nm fluorescent bead as a function of phase (shown in π radians on the x-axis). At a phase of 0.3 π radians, the tip is closest to the bead and the fluorescence is reduced or even minimized. When the tip is far from the bead the fluorescence is increased or even maximized. The tip is in a stationary X-Y position over the center of the 20 nm bead for a long time, e.g., ten seconds and more. The tip oscillates in the z (vertical) axis and the bead is continuously illuminated. In this combination of illumination (including phase and evanescent components) only a reduced detection rate is illustrated.

Figure 19:
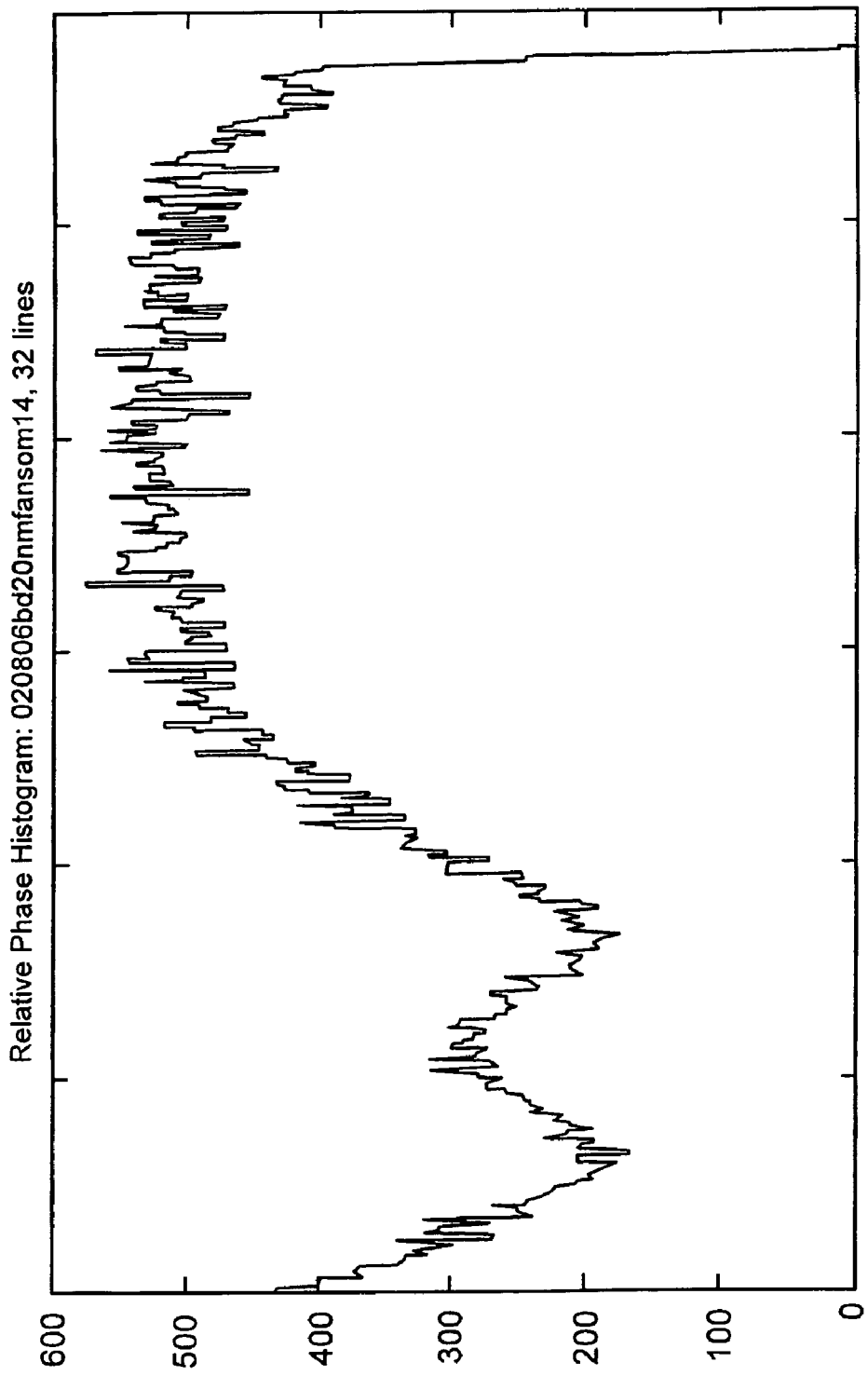

Another illustration is provided by the simplified diagram of FIG. 19, which plots photon count in the vertical axis against radians, i.e., phase, which are along the horizontal axis. A strong polarized evanescent component that has increased fluorescence is seen only when the tip is very close to the bead. At longer range the fluorescence is maximized as the tip to sample distance increases in a manner similar to that seen in FIG. 18.

Figure 20:
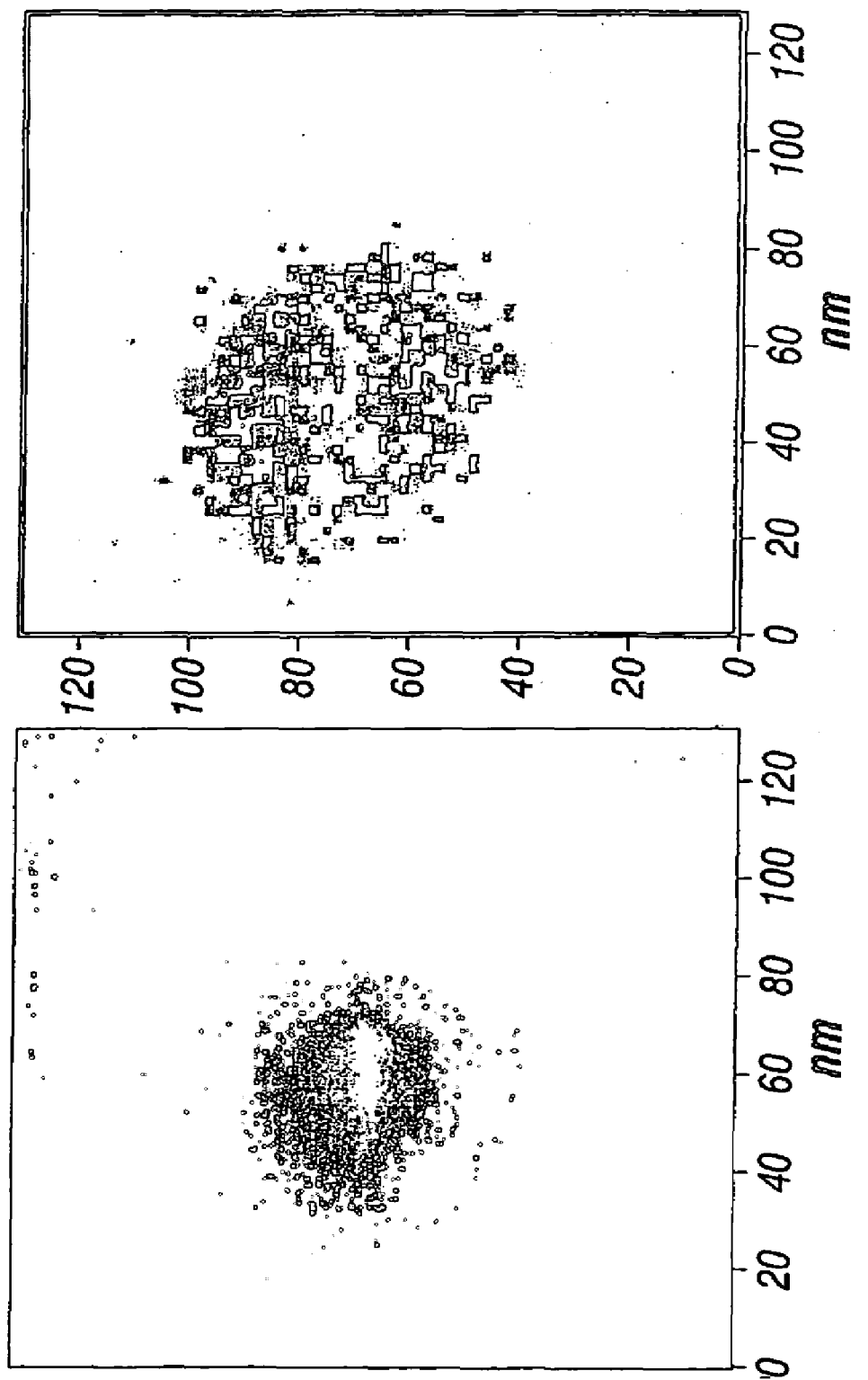
Figure 20A:
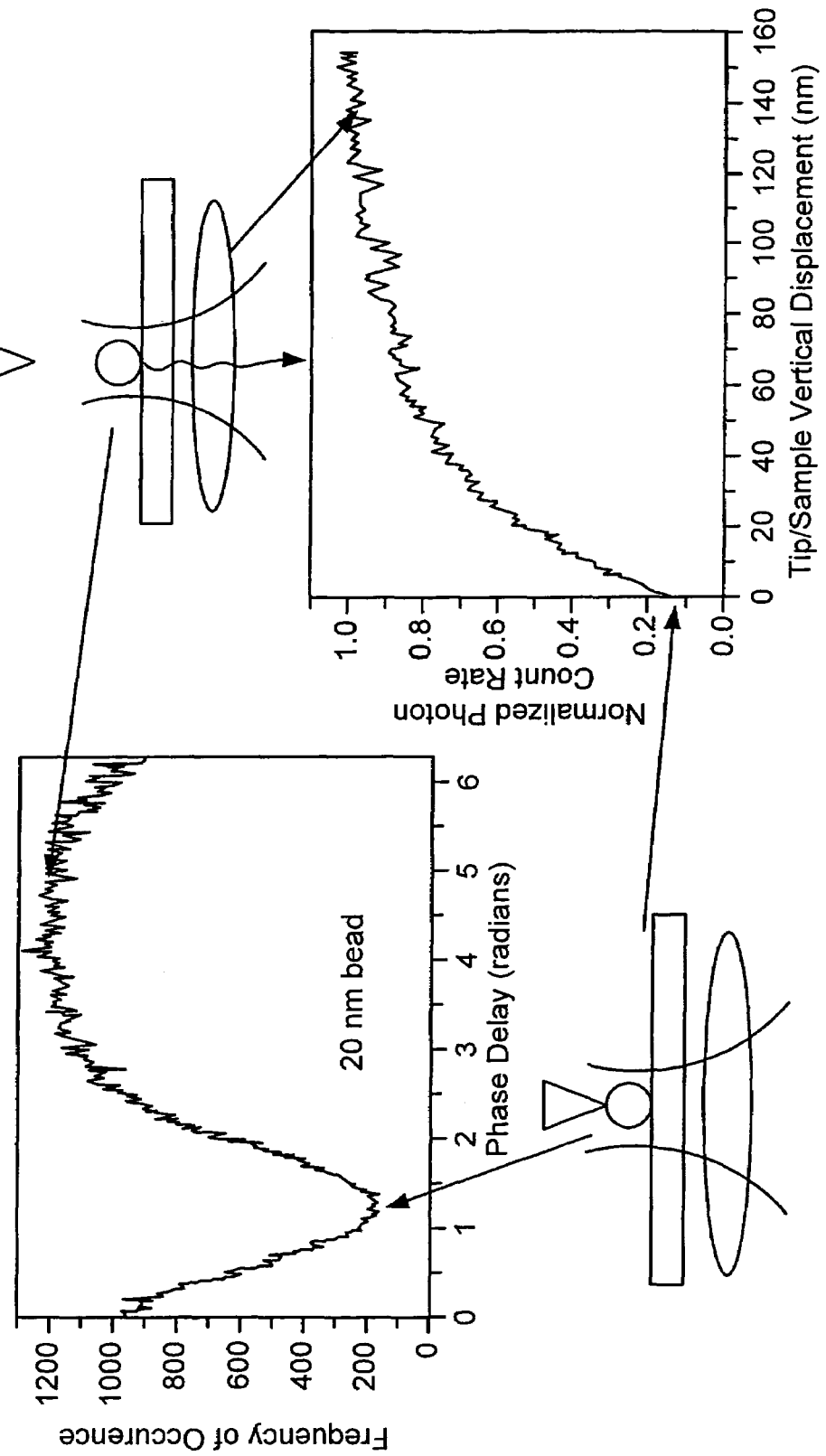
Figure 20B:
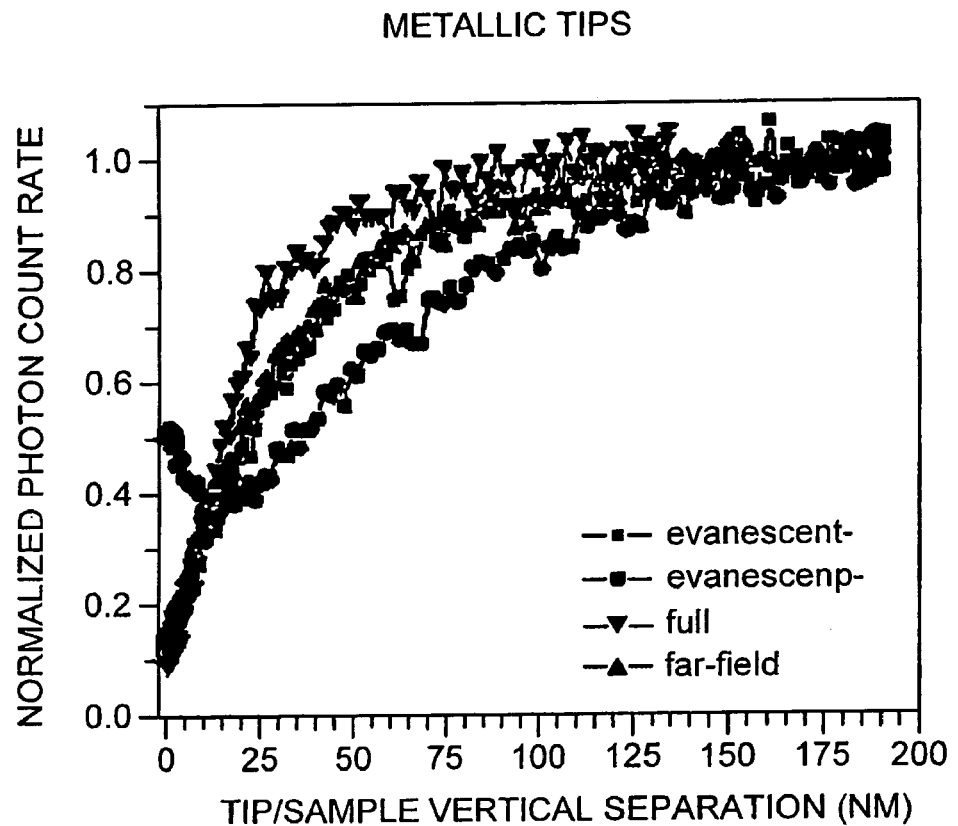

We also imaged the bead using AFM only and FANSOM. Referring to FIG. 20, the 20 nm fluorescent bead has been imaged by AFM (left) and FANSOM (right). The full width-half max (FWHM) diameter is measured on both images as 40 nm. The resolution of the FANSOM is therefore demonstrated to be at least 20 nm for this large sample. Accordingly, FANSOM resolution appears to be limited by the imaging capability of the probe and matches the best available via AFM. In other experiments, we prepared approach curves using a closed loop AFP (See, for example, FIGS. 20A and 20B), which provided improved positioning to a resolution of 10 nanometers and better. The closed loop AFM reduced or even minimized the relative drift of the probe over the sample. Partially by minimizing the relative drift error source, it can be expected that 10 nm resolution can be achieved using the present tips. In the present experiments, we used a NanoScope IV controller rather than the IIIa, which had been previously used. As noted above, we used the Digital Instruments BioScope with NanoScope IIIa controller to take the AFM image. Most of the presented FANSOM data was taken with the same optics coupled to a Closed-loop BioScope with NanoScope IV controller. The FANSOM resolution should improve with better probes (e.g. nanotubes) and smaller targets (e.g. quantum dots, biological molecules, etc.).

Figure 21:
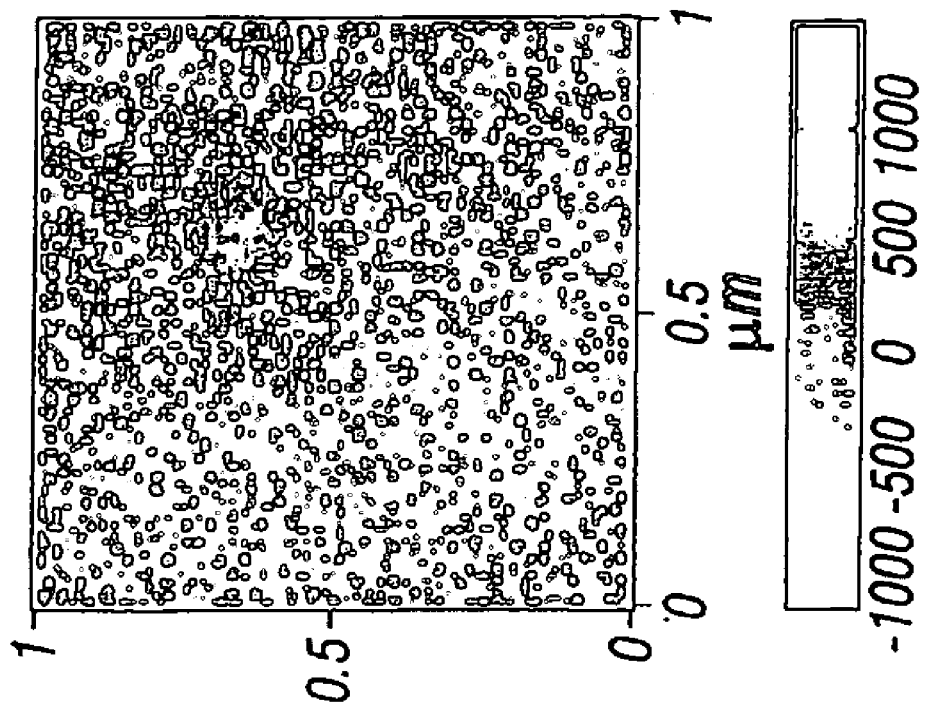
Figure 21:
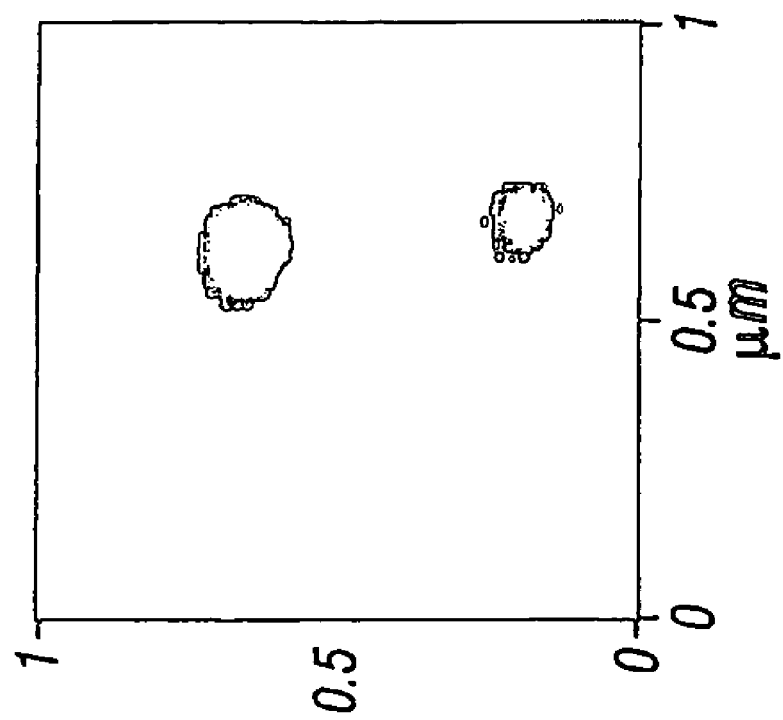

We also discovered that FANSOM can be used to distinguish different types of materials. For example, images of the bead and a dust particle have been captured. Such images are provided by the diagrams in FIG. 21. As shown, a 100 nm fluorescent bead and a dust particle are illustrated. On the left hand side using an AFM, the dust particle and bead are nearly indistinguishable (since they each appear as bright spots along a black background.) On the right hand side, they are imaged by FANSOM which clearly distinguishes the fluorescent spherical bead from the dust particle. Depending upon the embodiment, there can be many other variations, modifications, and alternatives.

Although the above has been illustrated in terms of specific hardware features, it would be recognized that many variations, alternatives, and modifications can exist. For example, any of the hardware features can be further combined, or even separated. The features can also be implemented, in part, through software or a combination of hardware and software. The hardware and software can be further integrated or less integrated depending upon the application. One of ordinary skill in the art would recognize many alternatives, variations, and modifications.

Figure 22:
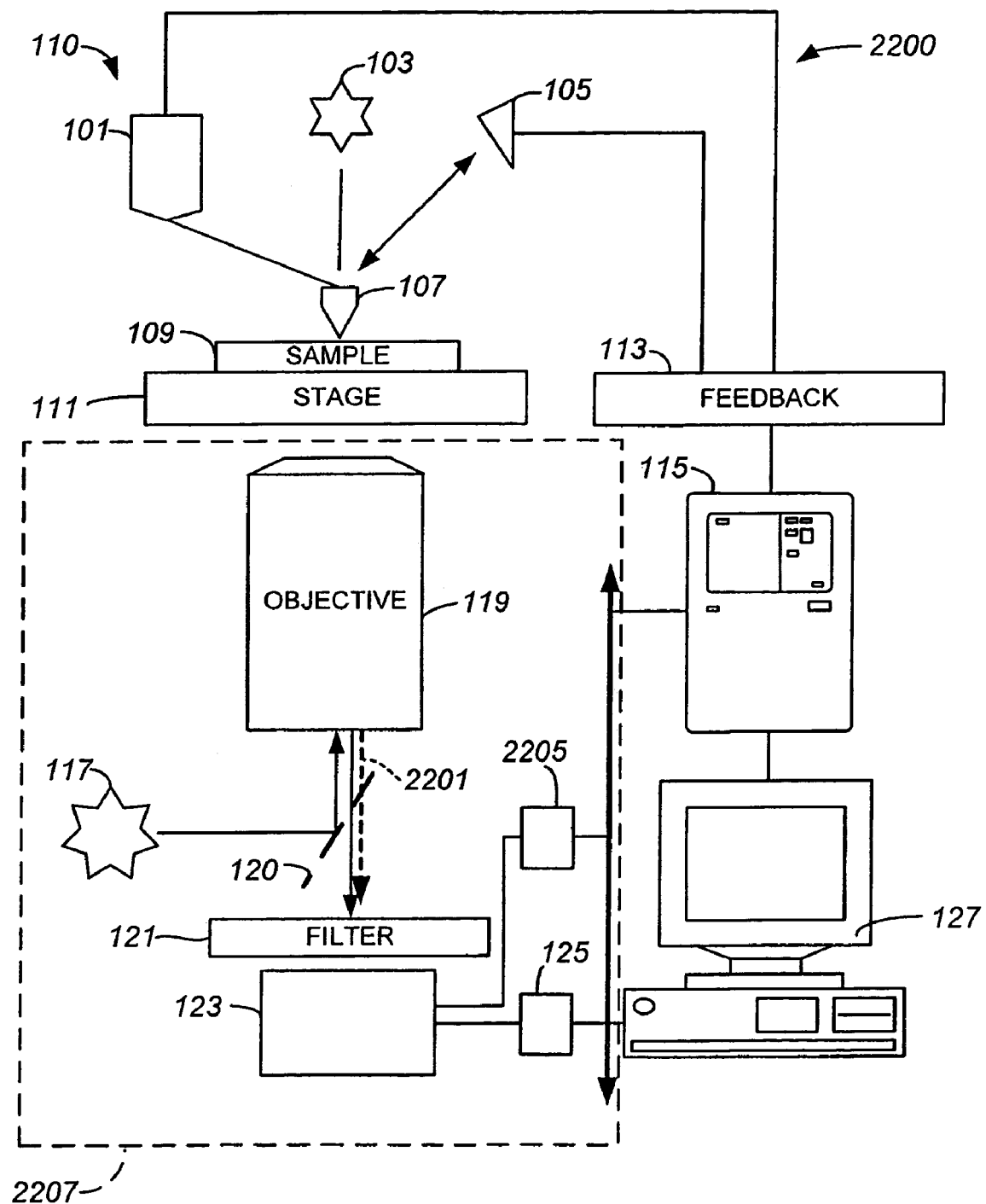
FIG. 22 is a simplified diagram of an alignment subsystem for an optical system according to an embodiment of the present invention.

FIG. 22 is a simplified diagram of an alignment subsystem 2200 for an optical system according to an embodiment of the present invention. This diagram is merely an example, which should not unduly limit the scope of the claims herein. One of ordinary skill in the art would recognize many other variations, modifications, and alternatives. As shown, a system 2200 for dynamically viewing an increased field of view based upon a smaller field of view to capture an image of features of samples to molecular sensitivity is included. Like reference numerals are used in this figure as the prior figures without limiting the scope of the claims herein. The system has an electromagnetic energy source (in a specific embodiment this can be a laser) 117, which is capable of emitting a beam. A fixed lens 119 is coupled to the electromagnetic energy source. The fixed lens focuses the beam toward at least one tip of a probe 107, which is in a vicinity of a feature of a sample to scatter a portion of the beam off a portion of the tip of the probe. A detector 2203 is coupled to the fixed lens. The detector detects the scattered portion of the beam. As shown, the scattered portion of the beam traverses through objective, through mirror 120, through filter (optional), to the detector. A processor 115 is coupled to the detector via input/output device 2205. The processor is adapted to process the scattered portion 2201 of the beam to determine a pattern to identify a relationship between the tip and the beam for a spatial alignment between the tip and the beam. As merely an example, conventional image processing techniques can be used. An adjustment device 111 is coupled to the processor. The adjustment device is adapted to adjust a position of the beam based upon at least the pattern to maintain a desired relationship between the tip and the beam. As merely an example, the adjustment device can be an x-y-z state or the like. Further details of the present system can be described with way of the following methods described below.

A method according to an embodiment of the present invention for dynamically viewing an increased field of view based upon a smaller fixed field of view to capture an image of features of samples to molecular sensitivity is provided as follows.

1. Output a beam from a laser coupled to an optical system, which is coupled to an AFM system;

2. Illuminate through a fixed lens coupled to the optical system using the beam of the laser a feature of a sample on a stage coupled to the AFM system;

3. Direct the beam toward at least one tip of a probe coupled to the AFM, which is in a vicinity of the feature of the sample;

4. Scatter a portion of the beam off a portion of the tip of the probe;

5. Traverse scattered portion through the fixed lens;

6. Detect the scattered portion of the beam using a detector;

7. Transfer signal indication from scattered portion being detected to a processor;

8. Process the signal indication of the scattered portion of the beam to determine a pattern to identify a relationship between the tip and the beam for spatial alignment between the tip and the beam;

9. If necessary, adjust a position of the beam used for illumination based upon at least the pattern to maintain a desired relationship between the tip and the beam; and 10. Maintain the alignment between the tip and the beam using one or more of the steps above.

These steps provide a way to align the probe tip of the AFM to the optical subsystem, which is coupled to the AFM. Such steps are provided as the AFM is operational or in-situ in some embodiments. These steps are used by way of a combination of computer hardware and/or software depending upon the embodiment. Further details of these steps are provided throughout this specification and more particularly below.

Figure 23:
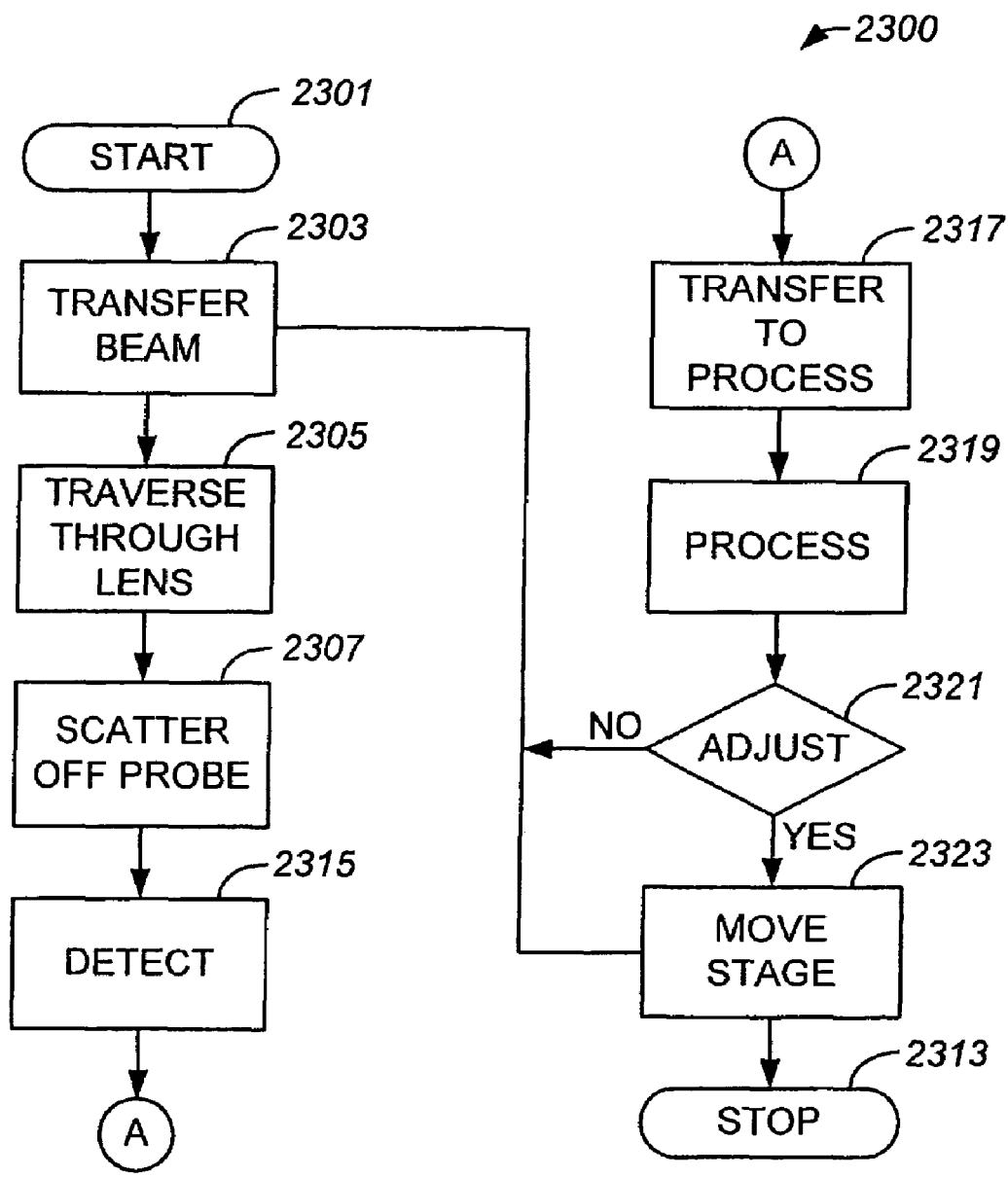
FIGS. 23 through 25 are simplified diagrams of tip detection alignment methods and systems for the scanning system according to embodiments of the present invention.
Figure 24:
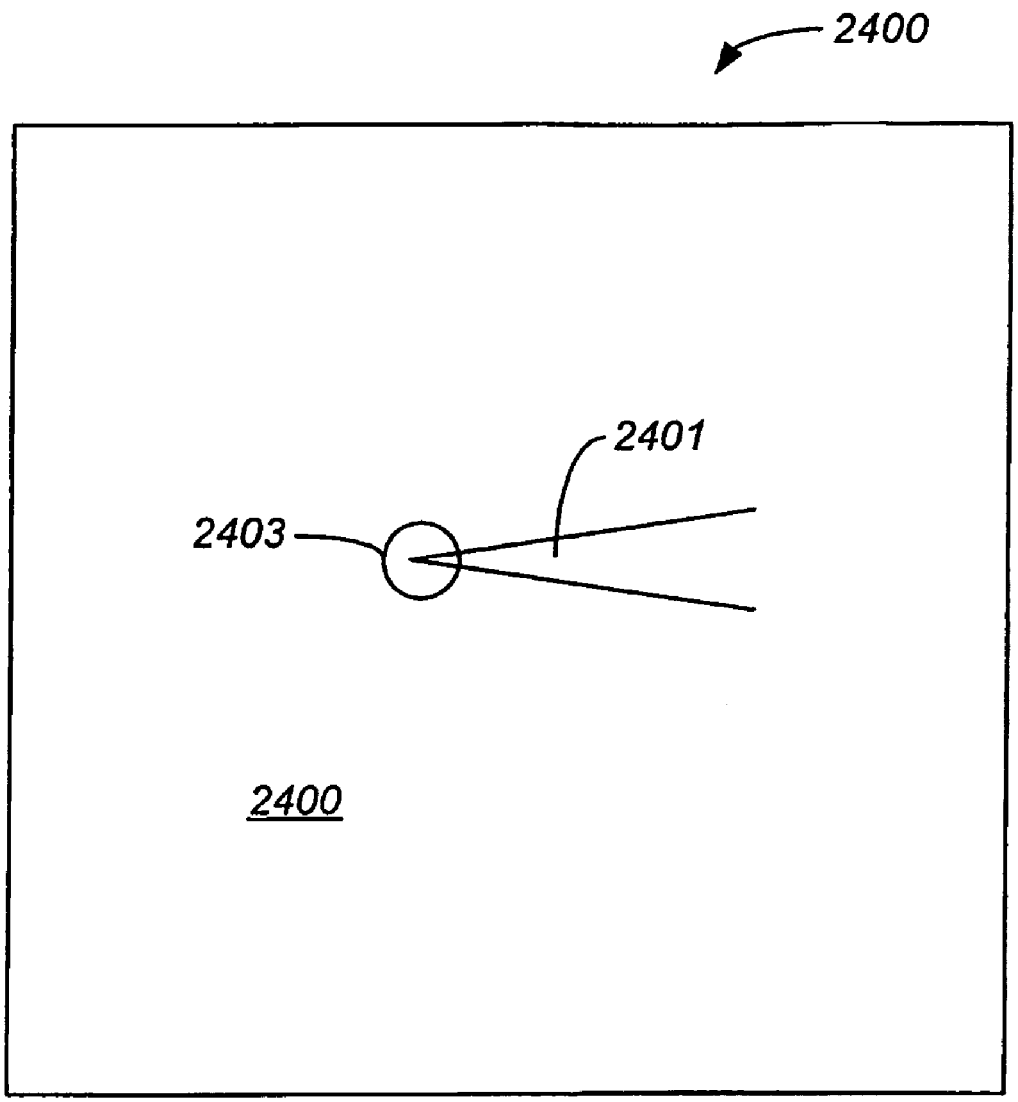

FIGS. 23 through 24 are simplified diagrams of tip detection alignment methods 2300 for the scanning system according to embodiments of the present invention. These diagrams are merely examples, which should not unduly limit the scope of the claims herein. One of ordinary skill in the art would recognize many other variations, modifications, and alternatives. The scanning system can be one or more of the ones that were previously described, as well as others. As shown, the method begins at start, step 2300. Here, the method for dynamically (e.g., moving) viewing an increased field of view based upon a smaller fixed field of view to capture an image of features of samples to molecular sensitivity. The method emits a beam from a laser for transfer, step 2303.

The method also includes illuminating (step 2305) through a fixed lens using the beam a feature of a sample. The beam is directed toward at least one tip of a probe, which is in a vicinity of the feature of the sample. Next, the method scatters (step 2307) a portion of the beam off a portion of the tip of the probe. The scattered beam traverses back through the lens. Optionally, the beam also scatters through a filter. The method detects (step 2315) the scattered portion of the beam using a detector. The detector can include a CCD camera, an avalanche photodiode, or the like.

The method then transfers (step 2317) signals associated with the detector to a processor. The method then processes (step 2319) the scattered portion of the beam to determine a pattern to identify a relationship between the tip and the beam for spatial alignment between the tip and the beam. The processing can be done on a conventional signal processor and/or computer or the like. The processor determines of the tip is aligned to the beam, step 2321. If so, the method continues to transfer the beam, which may have been continuously transferred, as the probe and sample move relative to each other in the scanning method. If not, the method adjusts (step 2323) a position of the beam used for illumination based upon at least the pattern to maintain a desired relationship between the tip and the beam. Such adjustment may occur using an automated x-y-z stage or the like. The method continues via the branch to step 2303. The method also stops at step 2313.

Referring to FIG. 24, the present method maintains alignment between the probe tip and laser beam. As noted above, such alignment is generally for precision measurement of the features of the sample. The probe tip 2401 should be aligned with the beam 2403, which can be viewed on display 2400. Such display can be coupled to the processor, which processes the signals of the image. Of course, there can be other modifications, alternatives and variations.

Figure 25:
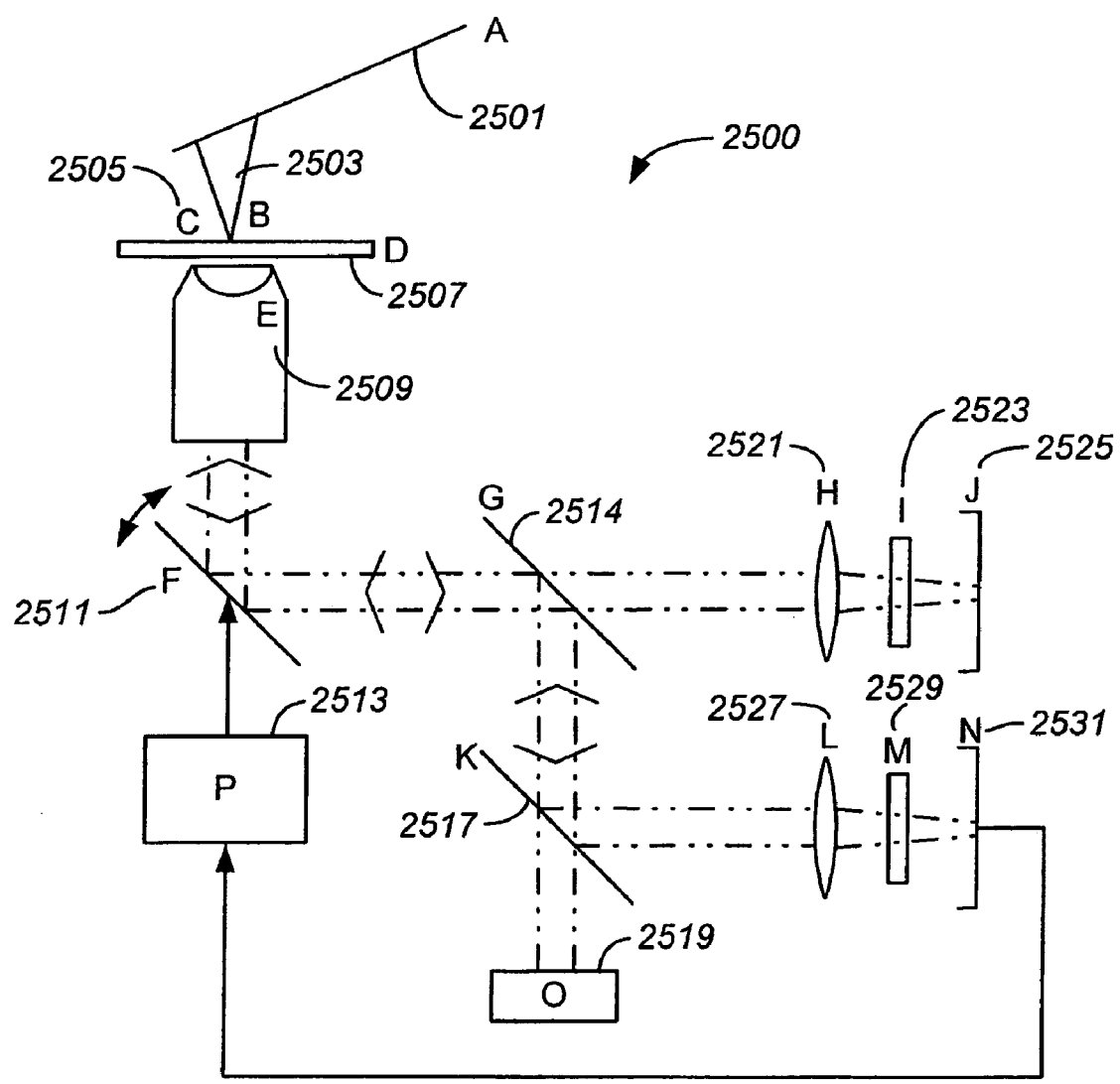

Preferably, the present method is provided on a secondary illumination system 2500, which is coupled to the FANSOM. Referring to FIG. 25, the system 2500 includes various elements, which can be found in the other systems described herein. Additionally, the system includes an independent or secondary illumination sub-system, which transmits and receives scattered light from the probe using a different wavelength of light than the main detector, which is used for the imaging. As shown, the system includes cantilever 2501, which is coupled to tip 2503. A sample 2505 such as a bead, fluorophore, DNA, quantum dot, or others is included. The sample is provided on cover slip 2507. An objective 2509 is coupled to the probe. A tip/tilt mirror 2511 directs light between dichroic mirror 2514 and objective. The dichroic mirror reflects an excitation laser and transmits the backscattered signal. As shown, the excitation laser 2519 transmits light through beam splitter 2517 to the mirror, which transmits the light to the probe. Such probe scatters light and directs it back through the secondary optical subsystem. The scattered light goes from the probe, through the objective, through a secondary eyepiece 2527, which is coupled to secondary bandpass filter 2529, which is coupled to a secondary detector 2531, which receives scattered light from the probe. The system also has primary eye piece 2521 coupled to primary filter 2523, which is coupled to primary detector 2525. Control electronics 2517 is coupled to the secondary detector 2531. The solid arrows and lines represent control signals and the other lines represent light paths. Of course, there can be many variations, alternatives, and modifications.

Although the above has been illustrated in terms of specific hardware and/or software features, it would be recognized that many variations, alternatives, and modifications can exist. For example, any of the hardware features can be further combined, or even separated. The features can also be implemented, in part, through software or a combination of hardware and software. The hardware and software can be further integrated or less integrated depending upon the application. One of ordinary skill in the art would recognize many alternatives, variations, and modifications.

Figure 25A:
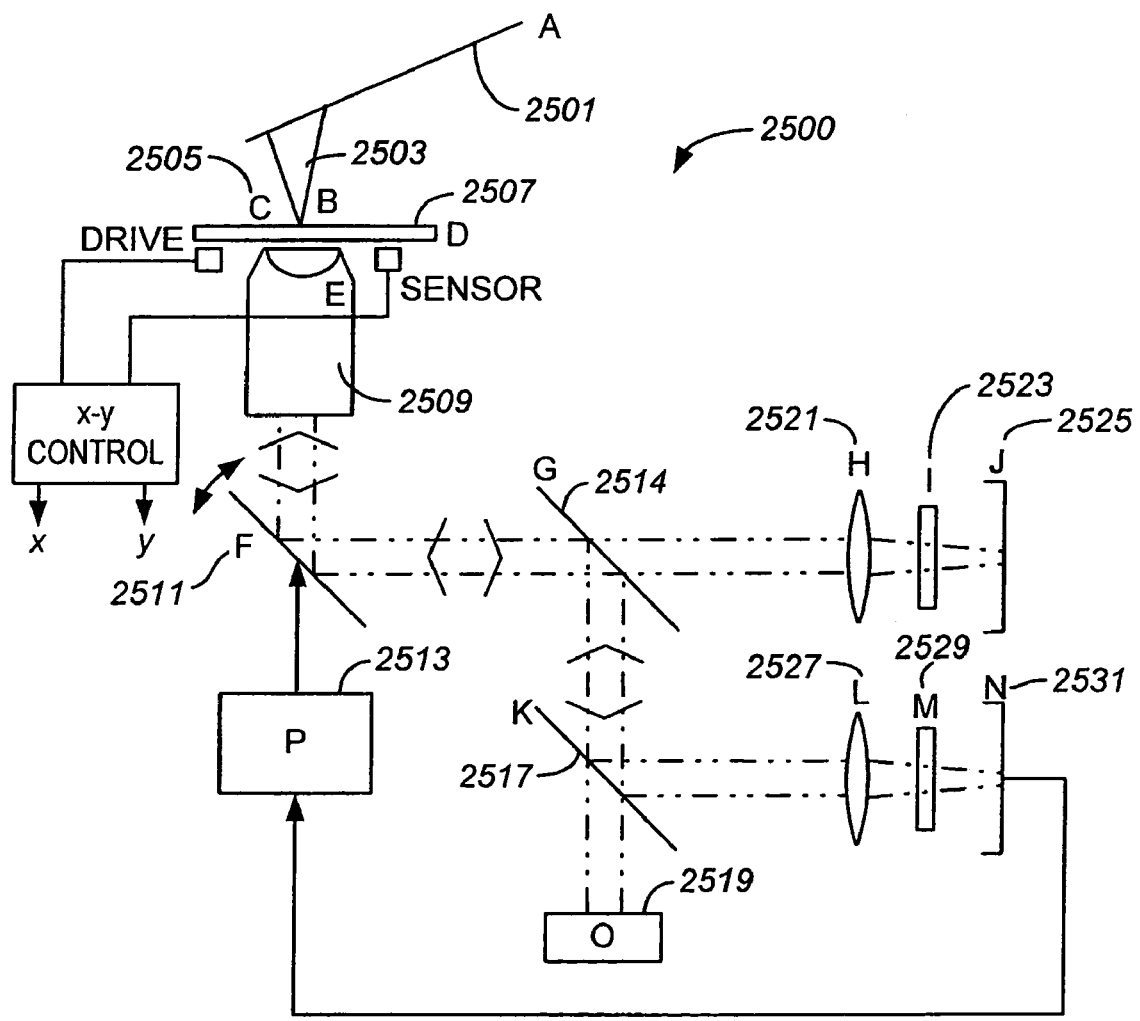
FIG. 25A is a simplified diagram of a FANSOM system using a closed loop feedback loop according to an embodiment of the present invention.
Figure 26:
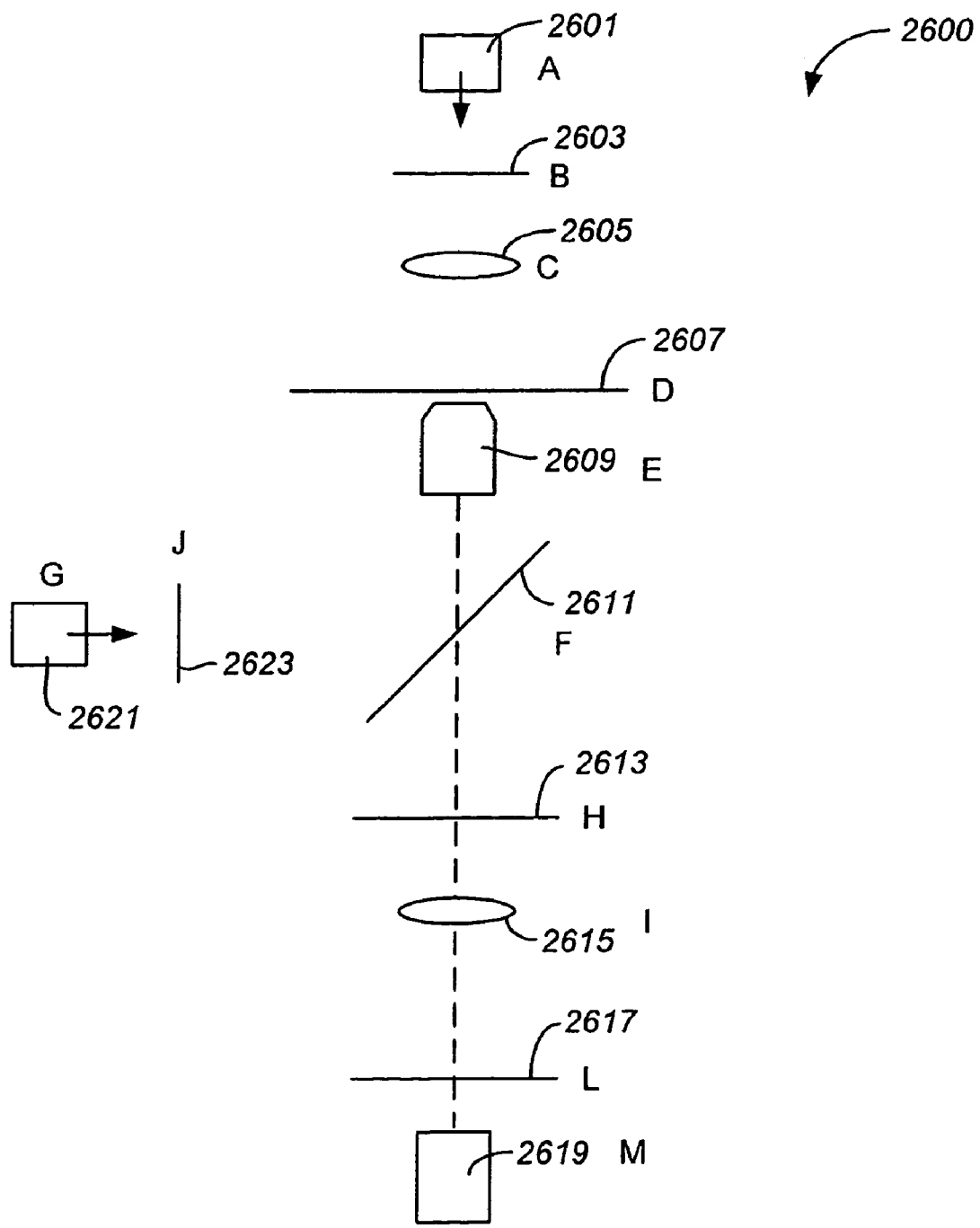
FIGS. 26 through 34 are simplified diagrams of methods and systems for selectively illuminating one or more samples according to embodiments of the present invention.

FIG. 25A is a simplified diagram of a FANSOM system using a closed loop feedback loop according to an embodiment of the present invention. This diagram is merely an example, which should not unduly limit the scope of the claims herein. One of ordinary skill in the art would recognize many other limitations, variations, and modifications. Preferably, the system includes use of a closed-loop AMF position information directly in combination with the tip-tilt mirror position information to maintain alignment while scanning large fields of view or while taking a series of high resolution small FOV images of many samples spread over a larger area (e.g. a 100 micron square region).

According to a specific embodiment to maintain the initial alignment while imaging a series of samples. Alignment established as above, both are commanded to new location, maintaining the earlier established alignment, then imaging commences as above. The location of each of these series of samples could be determined before either by patterning, by taking a large FOV image (for example using a CCD array) and determining the coordinates of each sample within the image, or by taking an AFM image of the sample and determining the coordinates of each sample. The series of sample coordinates then are used to direct both the closed-loop AFM and the tip-tilt mirror such that the sample is illuminated while maintaining alignment with the probe tip. A high resolution, high sensitivity image can then be taken of each sample in sequence.

Alternately, after achieving alignment, the closed loop AFM can be used to image a large FOV. The position information from the closed loop head can then be used to direct the tip-tilt mirror in such a manner as to maintain alignment as the area to be imaged is rastered over. In an alternate configuration the tip-tilt mirror is commanded to image a large FOV and the position information is used to direct the closed-loop AFM such that alignment is maintained between the probe tip and the excitation laser. Of course, there can be many variations, alternatives, and modifications depending upon the embodiment.

FIGS. 26 through 34 are simplified diagrams of methods and systems for selectively illuminating one or more samples according to embodiments of the present invention. These diagrams are merely examples, which should not unduly limit the scope of the claims herein. One of ordinary skill in the art would recognize many other variations, modifications, and alternatives. As shown, the system includes, among other elements, an AFM source (e.g., laser diode) 2601. The source is characterized by a certain wavelength of such as $\lambda_A$. A clean up filter 2603 is disposed between the source and a focusing lens 2605. The system includes a plane 2607 for a sample. The plane can be provided on a stage, e.g., x-y stage. The system includes a microscope objective 2609 underlying the sample stage for detecting one or more features from the sample. Other elements include a dichroic mirror 2611 coupled to a laser 2621 $\lambda_E$ for sample excitation. A clean up filter 2623 is disposed between the laser and dichroic mirror. The system also includes detector elements such as blocking filter for wavelength $\lambda_A$ between lens for sample imaging and dichroic mirror. A blocking filter is disposed between the lens and a sample detector 2617. Depending upon the embodiment, there can also be other elements. Details with regard to the operation of the system can be illustrated by FIGS. 27 through 34, which are simplified illustrations.

Figure 27:
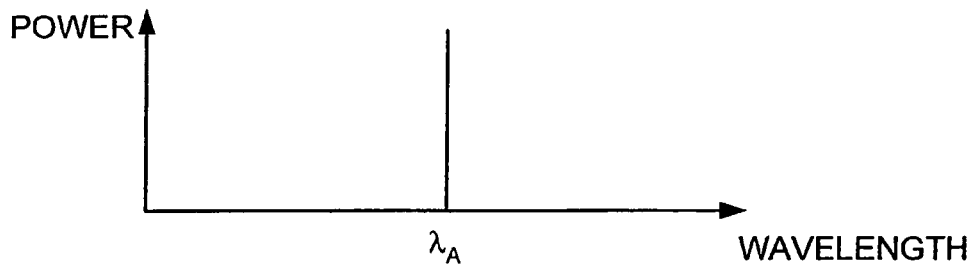
Figure 28:
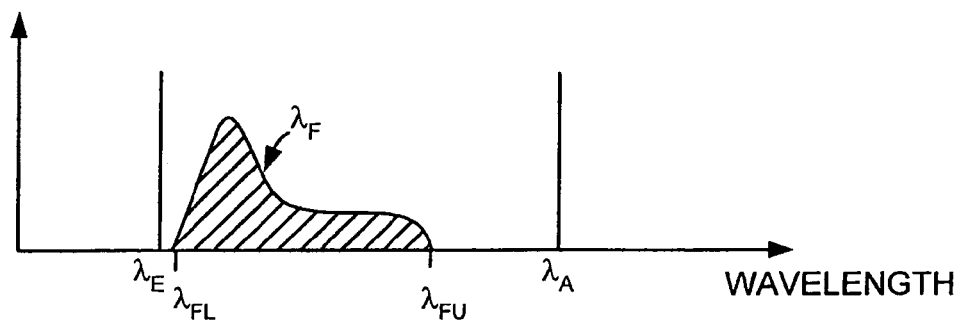
Figure 29:
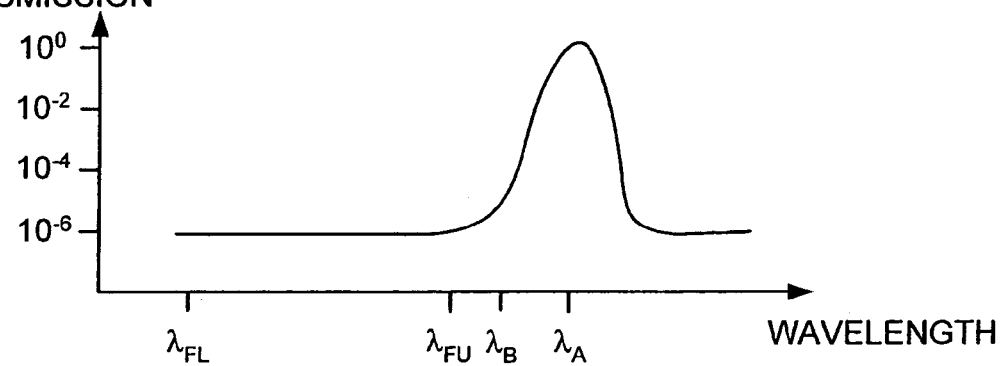
Figure 30:
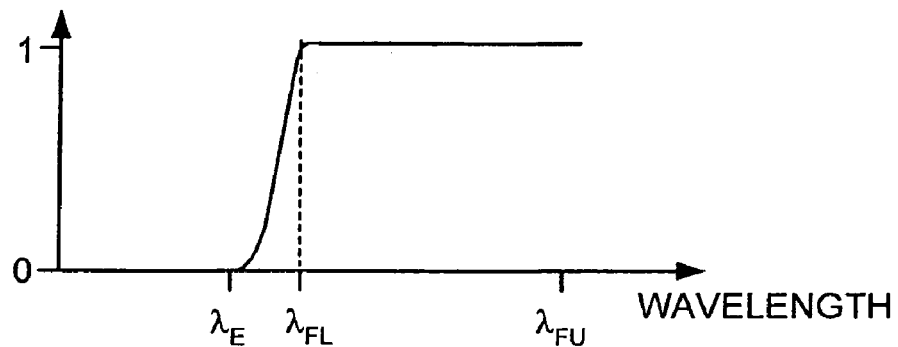
Figure 31:
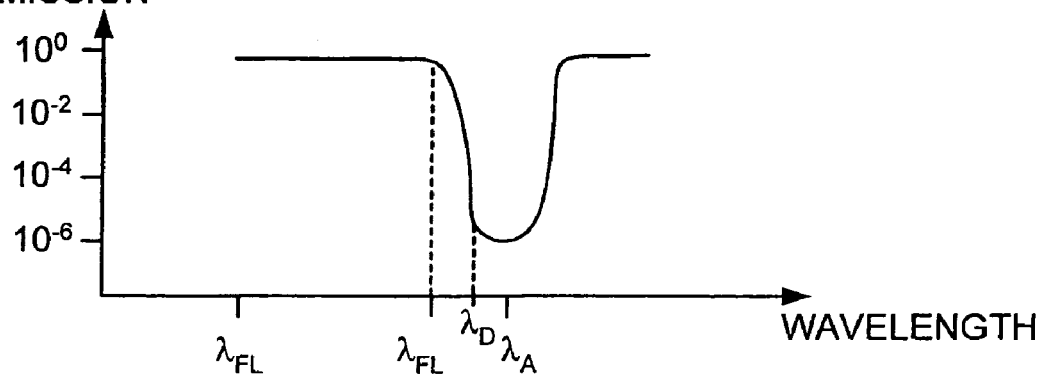
Figure 32:
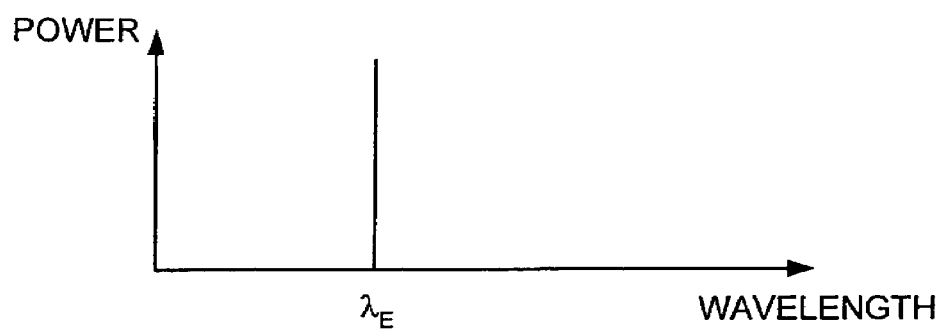
Figure 33:
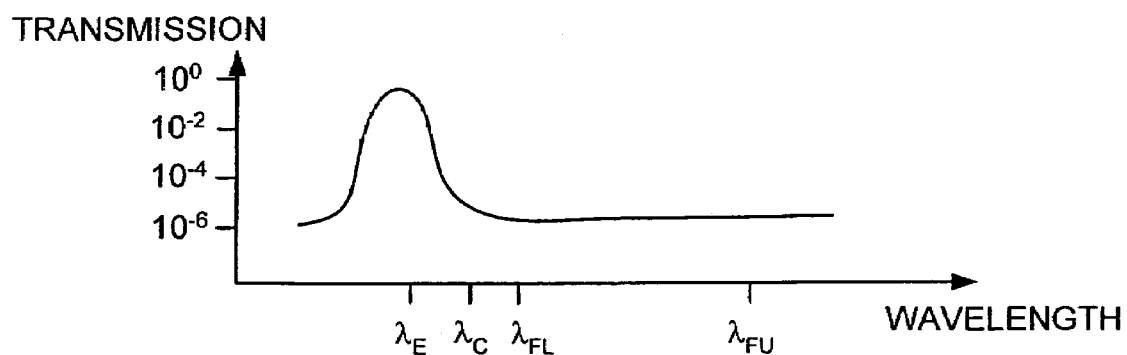
Figure 34:
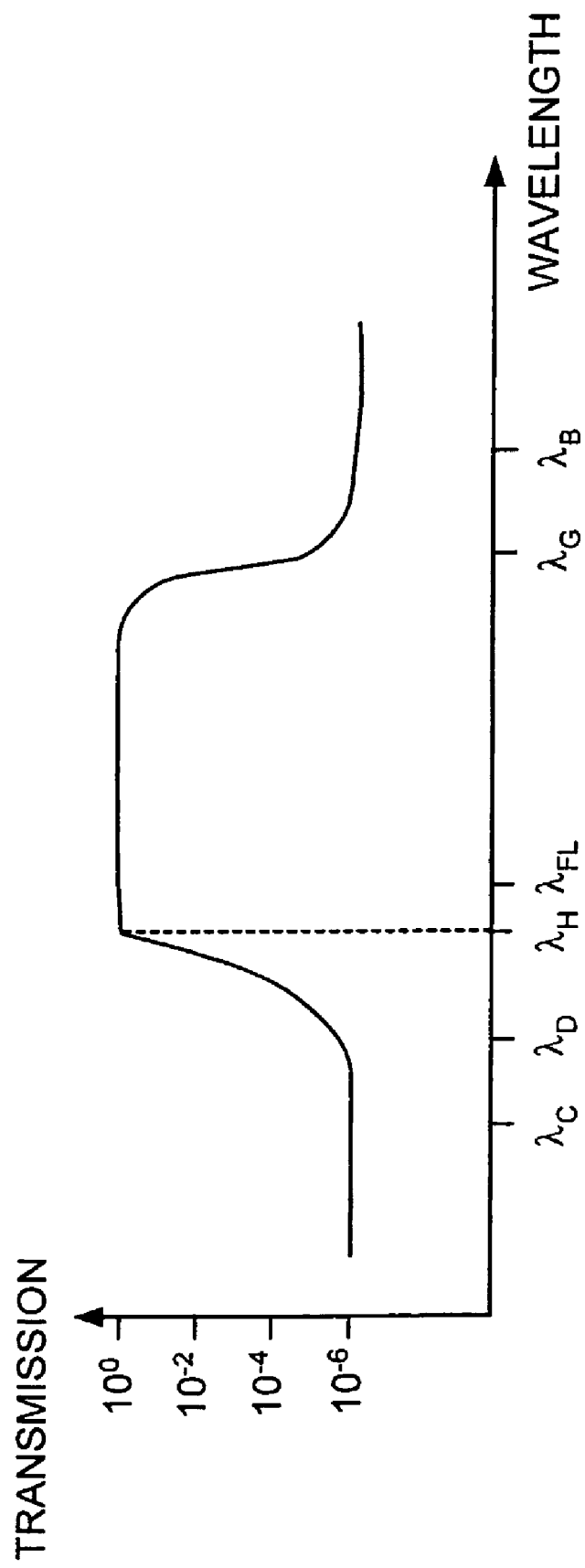

FIG. 27 is a simplified plot of power against wavelength for a spectrum of the AFM laser according to an embodiment of the present invention. The wavelength of the peak emission of the AFM laser is $\lambda_A$. FIG. 28 is a simplified plot of power against wavelength for relative positions of wavelengths of predetermined interest. Here, wavelength parameters are defined by $\lambda_E$ that corresponds to the wavelength of the peak emission from excitation laser, $\lambda_F$ that corresponds to a range of wavelengths emitted by a sample, $\lambda_{FL}$ that corresponds to a lower bound of a sample fluorescence, and $\lambda_{FU}$ that corresponds to an upper bound of a sample fluorescence. FIG. 29 is a simplified plot of transmission plotted against wavelength for a transmission spectrum of the ASE filter according to an embodiment of the present invention. Here, $\lambda_B$ is the wavelength at which transmission is down to about $10^{-5}$ and $\lambda_B$ is higher than $\lambda_{FU}$. FIG. 30 is a simplified plot of transmittivity plotted against wavelength for a transmission spectrum of a dichroic mirror according to an embodiment of the present invention. Here, certain characteristics are reflected at (rather than absorption) and transmission from FIG. 31 is a simplified plot of transmission plotted against wavelength for a blocking filter for a wavelength $\lambda_A$, which corresponds to a wavelength at which transmission falls to about $10^{-5}$ and $\lambda_B$ is higher than $\lambda_{FU}$. FIG. 32 is a simplified diagram illustrating power plotted against wavelength for a spectrum of a laser for sample excitation. As shown, $\lambda_E$ has been illustrated as a single peak. FIG. 33 is a simplified plot of transmission plotted against wavelength of an excitation clean-up filter according to an embodiment of the present invention. Here, $\lambda_C$ corresponds to a wavelength at which transmission falls to $10^{-5}$ and $\lambda_C$ is lower than $\lambda_{FL}$. FIG. 34 is a simplified plot of transmission as a function of wavelength. Here, $\lambda_J$ corresponds to a wavelength at which transmission is about $10^{-5}$ and $\lambda_J$ is higher than $\lambda_C$. Here, $\lambda_H$ corresponds to a wavelength at which transmission is about 60% and $\lambda_H$ is lower than $\lambda_{FL}$. Here, $\lambda_G$ corresponds to a wavelength at which transmission is about $10^{-5}$ and $\lambda_G$ is lower than $\lambda_B$ and also lower than $\lambda_D$. Of course, there can be other modifications, alternatives, and variations depending upon the embodiment.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method for measuring a characteristic of biological or chemical objects using detection of photons associated with biological or chemical objects, the method comprising:

providing a liquid environment;

providing a tip of a probe to be movable toward a feature of a biological or chemical sample in the liquid or gas environment to influence an emission of electromagnetic energy associated with the feature of the sample, the feature and the sample being maintained on a stage;

illuminating the tip of the probe using electromagnetic energy comprising a first intensity level as the tip of the probe moves toward the feature of the sample;

capturing a first signal associated with the feature during a first portion of movement of the tip during a portion of time associated with illuminating the tip of the probe with the electromagnetic energy comprising the first intensity level;

moving the tip of the probe using a tapping mode operation toward a vicinity of the feature of the sample during a second portion of movement of the tip;

providing electromagnetic energy comprising a second intensity level associated with the feature of the sample as the tip of the probe moves toward the vicinity of the feature of the sample during the second portion of movement of the tip to cause enhancement of the tip of the probe to the second intensity level;

determining a spatial coordinate of the stage on which the sample has maintained;

determining a distance of the tip of the probe relative to the feature of the sample; and capturing a second signal associated with the feature to create an image of the feature of the sample.

2. The method of claim 1 wherein the second intensity level is associated with an enhancement or quenching influence of the feature of the sample.

3. The method of claim 1 wherein the first portion and the second portion are provided within an oscillation cycle of the tip of the probe.

4. The method of claim 3 wherein the oscillation cycle is characterized by a predetermined frequency.

5. The method of claim 1 wherein the second intensity level is lower than the first intensity level.

6. The method of claim 1 wherein the vicinity of the feature is when the tip is in contact with the feature.

7. The method of claim 1 wherein the capturing the first signal and the capturing the second signal are among a plurality of capturing steps.

8. The method of claim 1 further comprising scanning the tip of the probe along a spatial surface region of the sample.

9. The method of claim 1 wherein the first signal is associated with a plurality of photons emitted from the feature of the sample.

10. The method of claim 1 wherein the second signal is associated with a plurality of photons emitted from the feature of the sample, the second signal being greater than the first signal.

11. The method of claim 1 further comprising using the probe for capturing information from the biological or chemical sample using an AFM mode of operation.

12. The method of claim 1 further comprising using the probe for capturing information from the biological or chemical sample using an AFM mode of operation or a FANSOM mode of operation.

* * * * *